US 7,074,179 B2

(12) United States Patent
Wang et al.

(10) Patent No.: US 7,074,179 B2
(45) Date of Patent: **\*Jul. 11, 2006**

(54) METHOD AND APPARATUS FOR PERFORMING MINIMALLY INVASIVE CARDIAC PROCEDURES

(75) Inventors: Yulun Wang, Goleta, CA (US); Darrin R. Uecker, Santa Barbara, CA (US); Keith Phillip Laby, Santa Barbara, CA (US); Jeff Wilson, Santa Barbara, CA (US); Steve Jordan, Santa Barbara, CA (US); James Wright, Santa Barbara, CA (US)

(73) Assignee: Intuitive Surgical Inc, Sunnyvale, CA (US)

( * ) Notice: Subject to any disclaimer, the term of this patent is extended or adjusted under 35 U.S.C. 154(b) by 248 days.

This patent is subject to a terminal disclaimer.

(21) Appl. No.: 10/241,143

(22) Filed: Sep. 10, 2002

(65) Prior Publication Data

US 2003/0060809 A1 Mar. 27, 2003

Related U.S. Application Data

(63) Continuation of application No. 09/000,934, filed on Dec. 30, 1997, now Pat. No. 6,905,491, which is a continuation-in-part of application No. 08/903,914, filed on Jul. 31, 1997, now Pat. No. 5,815,640, which is a continuation of application No. 08/613,866, filed on Mar. 11, 1996, now Pat. No. 5,907,664, which is a continuation of application No. 08/072,982, filed on Jun. 3, 1993, now Pat. No. 5,524,180, which is a continuation-in-part of application No. 08/005,604, filed on Jan. 19, 2003, now abandoned, which is a continuation-in-part of application No. 07/927,801, filed on Aug. 10, 1992, now abandoned.

(51) Int. Cl.
*A61B 1/00* (2006.01)

(52) U.S. Cl. ............... 600/101; 600/102; 600/103; 600/104; 600/118; 606/10; 606/41; 606/46; 901/2; 901/14; 901/30; 901/36; 901/46; 414/2

(58) Field of Classification Search ............... 606/1, 606/10, 11, 13, 41, 43, 106, 107, 130, 46; 600/101–104, 106–109, 114, 118; 704/3, 704/200–210, 231; 901/2, 6, 8–10, 14–18, 901/30, 36, 46; 414/2
See application file for complete search history.

(56) References Cited

U.S. PATENT DOCUMENTS 977,825 A   12/1910   Murphy (Continued)

FOREIGN PATENT DOCUMENTS

DE        9204118.3 U1      7/1992

(Continued)

OTHER PUBLICATIONS

ABSTRACT of a presentation "A Pneumatic Controlled Sewing Device for Endoscopic Application the MIS Sewing Instrument MSI" given at the 3rd World Congress of Endoscopic Surgery in Bordeaux, Jun. 18–20, 1992 (1 page total).

(Continued)

*Primary Examiner*—A. Farah

(57) ABSTRACT

A robotic system that moves a surgical instrument in response to the actuation of a foot pedal that can be operated by the foot of a surgeon. The robotic system has an end effector that is adapted to hold a surgical instrument such as an endoscope. The end effector is coupled to a robotic arm assembly which can move the endoscope relative to the patient. The system includes a computer which controls the movement of the robotic arm in response to input signals received from the foot pedal.

21 Claims, 11 Drawing Sheets

U.S. PATENT DOCUMENTS

| | | | |
|---|---|---|---|
| 3,171,549 A | 3/1965 | Orloff | |
| 3,280,991 A | 10/1966 | Melton et al. | |
| 3,710,798 A * | 1/1973 | Bredemeier | 606/11 |
| 4,058,001 A | 11/1977 | Waxman | |
| 4,128,880 A | 12/1978 | Cray, Jr. | |
| 4,221,997 A | 9/1980 | Flemming | |
| 4,367,998 A | 1/1983 | Causer | |
| 4,401,852 A | 8/1983 | Noso et al. | |
| 4,456,961 A | 6/1984 | Price et al. | |
| 4,460,302 A | 7/1984 | Moreau et al. | |
| 4,474,174 A | 10/1984 | Petruzzi | |
| 4,491,135 A | 1/1985 | Klein | |
| 4,503,854 A | 3/1985 | Jako | |
| 4,517,963 A | 5/1985 | Michel | |
| 4,523,884 A | 6/1985 | Clement et al. | |
| 4,586,398 A | 5/1986 | Yindra | |
| 4,604,016 A | 8/1986 | Joyce | |
| 4,616,637 A | 10/1986 | Caspari et al. | |
| 4,624,011 A | 11/1986 | Watanabe et al. | |
| 4,633,389 A | 12/1986 | Tanaka et al. | |
| 4,635,292 A | 1/1987 | Mori et al. | |
| 4,635,479 A | 1/1987 | Salisbury, Jr. et al. | |
| 4,641,292 A | 2/1987 | Tunnell et al. | |
| 4,655,257 A | 4/1987 | Iwashita | |
| 4,672,963 A | 6/1987 | Barken | |
| 4,676,243 A | 6/1987 | Clayman | |
| 4,728,974 A | 3/1988 | Nio et al. | |
| 4,762,455 A | 8/1988 | Coughlan et al. | |
| 4,791,934 A | 12/1988 | Brunnett | |
| 4,791,940 A | 12/1988 | Hirschfeld et al. | |
| 4,794,912 A | 1/1989 | Lia | |
| 4,815,006 A | 3/1989 | Andersson et al. | |
| 4,815,450 A | 3/1989 | Patel | |
| 4,837,734 A | 6/1989 | Ichikawa et al. | |
| 4,852,083 A | 7/1989 | Niehaus et al. | |
| 4,853,874 A | 8/1989 | Iwamoto et al. | |
| 4,854,301 A | 8/1989 | Nakajima | |
| 4,860,215 A | 8/1989 | Seraji | |
| 4,863,133 A | 9/1989 | Bonnell | |
| 4,883,400 A | 11/1989 | Kuban et al. | |
| 4,930,494 A | 6/1990 | Takehana et al. | |
| 4,945,479 A | 7/1990 | Rusterholz et al. | |
| 4,949,717 A | 8/1990 | Shaw | |
| 4,954,952 A | 9/1990 | Ubhayakar et al. | |
| 4,965,417 A | 10/1990 | Massie | |
| 4,969,709 A | 11/1990 | Sogawa et al. | |
| 4,969,890 A | 11/1990 | Sugita et al. | |
| 4,979,933 A | 12/1990 | Runge | |
| 4,979,949 A | 12/1990 | Matsen, III et al. | |
| 4,980,626 A | 12/1990 | Hess et al. | |
| 4,989,253 A | 1/1991 | Liang et al. | |
| 4,996,975 A | 3/1991 | Nakamura | |
| 5,019,968 A | 5/1991 | Wang et al. | |
| 5,020,001 A | 5/1991 | Yamamoto et al. | |
| 5,046,375 A | 9/1991 | Salisbury, Jr. et al. | |
| 5,060,632 A | 10/1991 | Hibino et al. | |
| 5,065,741 A | 11/1991 | Uchiyama et al. | |
| 5,078,140 A | 1/1992 | Kwoh | |
| 5,086,401 A | 2/1992 | Glassman et al. | |
| 5,091,656 A | 2/1992 | Gahn | |
| 5,097,829 A | 3/1992 | Quisenberry | |
| 5,097,839 A | 3/1992 | Allen | |
| 5,098,426 A | 3/1992 | Sklar et al. | |
| 5,105,367 A | 4/1992 | Tsuchihashi et al. | |
| 5,109,499 A | 4/1992 | Inagami et al. | |
| 5,123,095 A | 6/1992 | Papadopoulos et al. | |
| 5,131,105 A | 7/1992 | Harrawood et al. | |
| 5,142,930 A | 9/1992 | Allen et al. | |
| 5,145,227 A | 9/1992 | Monford, Jr. | |
| 5,166,513 A | 11/1992 | Keenan et al. | |
| 5,175,694 A | 12/1992 | Amato | |
| 5,182,641 A | 1/1993 | Diner et al. | |
| 5,184,601 A | 2/1993 | Putman | |
| 5,187,574 A | 2/1993 | Kosemura et al. | |
| 5,196,688 A | 3/1993 | Hesse et al. | |
| 5,201,325 A | 4/1993 | McEwen et al. | |
| 5,201,743 A | 4/1993 | Haber et al. | |
| 5,217,003 A | 6/1993 | Wilk | |
| 5,221,283 A | 6/1993 | Chang | |
| 5,228,429 A | 7/1993 | Hatano | |
| 5,230,623 A | 7/1993 | Guthrie et al. | |
| 5,236,432 A | 8/1993 | Matsen, III et al. | |
| 5,251,127 A | 10/1993 | Raab | |
| 5,257,999 A | 11/1993 | Slanetz, Jr. | |
| 5,271,384 A | 12/1993 | McEwen et al. | |
| 5,279,309 A | 1/1994 | Taylor et al. | |
| 5,282,806 A | 2/1994 | Haber et al. | |
| 5,289,273 A | 2/1994 | Lang | |
| 5,289,365 A | 2/1994 | Caldwell et al. | |
| 5,299,288 A | 3/1994 | Glassman et al. | |
| 5,300,926 A | 4/1994 | Stoeckl | |
| 5,303,148 A | 4/1994 | Mattson et al. | |
| 5,304,185 A | 4/1994 | Taylor | |
| 5,305,203 A | 4/1994 | Raab | |
| 5,305,427 A | 4/1994 | Nagata | |
| 5,309,717 A | 5/1994 | Minch | |
| 5,313,306 A | 5/1994 | Kuban et al. | |
| 5,337,732 A | 8/1994 | Grundfest et al. | |
| 5,339,799 A | 8/1994 | Kami et al. | |
| 5,343,385 A | 8/1994 | Joskowicz et al. | |
| 5,343,391 A | 8/1994 | Mushabac | |
| 5,345,538 A | 9/1994 | Narayannan et al. | |
| 5,357,962 A | 10/1994 | Green | |
| 5,368,015 A | 11/1994 | Wilk | |
| 5,368,428 A | 11/1994 | Hussey et al. | |
| 5,371,536 A | 12/1994 | Yamaguchi | |
| 5,382,885 A | 1/1995 | Salcudean et al. | |
| 5,388,987 A | 2/1995 | Badoz et al. | |
| 5,395,369 A | 3/1995 | McBrayer et al. | |
| 5,397,323 A | 3/1995 | Taylor et al. | |
| 5,402,801 A | 4/1995 | Taylor | |
| 5,403,319 A | 4/1995 | Matsen, III et al. | |
| 5,408,409 A | 4/1995 | Glassman et al. | |
| 5,410,638 A | 4/1995 | Colgate et al. | |
| 5,417,210 A | 5/1995 | Funda et al. | |
| 5,417,701 A | 5/1995 | Holmes | |
| 5,422,521 A | 6/1995 | Neer et al. | |
| 5,431,645 A | 7/1995 | Smith et al. | |
| 5,434,457 A | 7/1995 | Josephs et al. | |
| 5,442,728 A | 8/1995 | Kaufman et al. | |
| 5,445,166 A | 8/1995 | Taylor | |
| 5,451,924 A | 9/1995 | Massimino et al. | |
| 5,455,766 A | 10/1995 | Scheller et al. | |
| 5,458,547 A | 10/1995 | Teraoka et al. | |
| 5,458,574 A | 10/1995 | Machold et al. | |
| 5,476,010 A | 12/1995 | Fleming et al. | |
| 5,483,961 A * | 1/1996 | Kelly et al. | 600/429 |
| 5,490,117 A | 2/1996 | Oda et al. | |
| 5,506,912 A | 4/1996 | Nagasaki et al. | |
| 5,512,919 A | 4/1996 | Araki | |
| 5,515,478 A | 5/1996 | Wang | |
| 5,524,180 A * | 6/1996 | Wang et al. | 600/118 |
| 5,544,654 A | 8/1996 | Murphy et al. | |
| 5,553,198 A | 9/1996 | Wang et al. | |
| 5,562,503 A | 10/1996 | Ellman et al. | |
| 5,571,110 A | 11/1996 | Matsen, III et al. | |
| 5,572,999 A | 11/1996 | Funda et al. | |
| 5,609,560 A | 3/1997 | Ichikawa et al. | |
| 5,626,595 A | 5/1997 | Sklar et al. | |
| 5,629,594 A | 5/1997 | Jacobus et al. | |
| 5,630,431 A | 5/1997 | Taylor | |

| | | |
|---|---|---|
| 5,631,973 A | 5/1997 | Green |
| 5,636,259 A | 6/1997 | Khutoryansky et al. |
| 5,649,956 A | 7/1997 | Jensen et al. |
| 5,657,429 A | 8/1997 | Wang et al. |
| 5,658,250 A | 8/1997 | Blomquist et al. |
| 5,695,500 A | 12/1997 | Taylor et al. |
| 5,696,574 A | 12/1997 | Schwaegerle |
| 5,696,837 A | 12/1997 | Green |
| 5,718,038 A | 2/1998 | Takiar et al. |
| 5,735,290 A | 4/1998 | Sterman et al. |
| 5,737,711 A | 4/1998 | Abe |
| 5,749,362 A | 5/1998 | Funda et al. |
| 5,754,741 A | 5/1998 | Wang et al. |
| 5,762,458 A | 6/1998 | Wang et al. |
| 5,776,126 A | 7/1998 | Wilk et al. |
| 5,779,623 A | 7/1998 | Bonnell |
| 5,800,423 A | 9/1998 | Jensen |
| 5,807,378 A | 9/1998 | Jensen et al. |
| 5,808,665 A | 9/1998 | Green |
| 5,810,880 A | 9/1998 | Jensen et al. |
| 5,813,813 A | 9/1998 | Daum et al. |
| 5,814,038 A | 9/1998 | Jensen et al. |
| 5,817,084 A | 10/1998 | Jensen |
| 5,825,982 A | 10/1998 | Wright et al. |
| 5,836,869 A | 11/1998 | Kudo et al. |
| 5,844,824 A | 12/1998 | Newman et al. |
| 5,859,934 A | 1/1999 | Green |
| 5,860,995 A | 1/1999 | Berkelaar |
| 5,878,193 A | 3/1999 | Wang et al. |
| 5,882,206 A | 3/1999 | Gillio |
| 5,887,121 A | 3/1999 | Funda et al. |
| 5,907,664 A * | 5/1999 | Wang et al. ............... 700/251 |
| 5,931,832 A | 8/1999 | Jensen |
| 5,950,629 A | 9/1999 | Taylor et al. |
| 6,024,695 A | 2/2000 | Taylor et al. |
| 6,102,850 A * | 8/2000 | Wang et al. ............... 600/102 |
| 6,120,433 A | 9/2000 | Mizuno et al. |
| 6,201,984 B1 * | 3/2001 | Funda et al. ............... 600/407 |
| 6,223,100 B1 * | 4/2001 | Green ....................... 700/264 |
| 6,231,526 B1 | 5/2001 | Taylor et al. |
| 6,236,875 B1 * | 5/2001 | Bucholz et al. ............ 600/407 |
| 6,259,806 B1 | 7/2001 | Green |
| 6,278,975 B1 | 8/2001 | Brant et al. |
| 6,490,475 B1 * | 12/2002 | Seeley et al. ............... 600/426 |
| 6,574,355 B1 * | 6/2003 | Green ....................... 382/128 |

FOREIGN PATENT DOCUMENTS

| | | |
|---|---|---|
| EP | 0239409 A1 | 9/1987 |
| EP | 0424687 A1 | 5/1991 |
| EP | 0 776 738 A1 | 6/1997 |
| WO | WO 91/04711 | 4/1991 |
| WO | WO 93/13916 | 7/1993 |
| WO | WO 94/18881 A1 | 9/1994 |
| WO | WO 94/26167 A1 | 11/1994 |
| WO | WO 97/15240 A1 | 5/1997 |
| WO | WO 98/25666 A1 | 6/1998 |

OTHER PUBLICATIONS

ABSTRACT of a presentation given at the 3rd World Congress of Endoscopic Surgery in Bordeaux, Jun. 18–20, 1992, (Session 15/1) (1 page total).

ABSTRACT of a presentation given at the 3rd World Congress of Endoscopic Surgery in Bordeaux (Jun. 18 to 20, 1992), (Session 15/2), (1 page total).

ABSTRACT of a presentation "3–D Vision Technology Applied to Advanced Minimally Invasive Surgery Systems" (Session 15/3) given at the 3rd World Congress of Endoscopic Surgery in Bordeaux, Jun. 18–20, 1992 (1 page total).

ABSTRACT of a presentation given at the 3rd World Congress of Endoscopic Surgery in Bordeaux (Jun. 18 to 20, 1992), (Session 15/4) (1 page total).

ABSTRACT of a presentation given at the 3rd World Congress of Endoscopic Surgery in Bordeaux (Jun. 18 to 20, 1992), (Session 15/5) (1 page total).

Bejczy, "Controlling Remote Manipulators through Kinesthetic Coupling," Computers in Mechanical Engineering 1983, pp. 48–60.

Besant et al., Abstract of a presentation "Camera Control for Laparoscopic Surgery by Speech–Recognizing Robot: Constant Attention and Better Use of Personnel," given at the 3rd World Congress of Endoscopic Surgery in Bordeaux, Jun. 18–20, 1992 (1 page total).

Charles et al., "Design of a Surgeon–Machine Interface for Teleoperated Microsurgery," *IEEE* 1989 (3 pages total).

Colgate, "Power and Impedance Scaling in Bilateral Manipulation," *IEEE*, 1991, pp. 2292–2297.

Corcoran, "Robots for the Operating Room," The New York Times, Sunday Jul. 19, 1992, Section 3, p. 9, col. 1 (2 pages total).

Das et al., "Kinematic Control and Visual Display of Redundant Teleoperators," *IEEE*, International Conference on Systems, Man, and Cybernetics Nov. 14–17, 1989, Cambridge, MA (published Feb. 1989) pp. 1072–1077.

Dolan et al., "A Robot in an Operating Room: A Bull in a China Shop," *IEEE*, 1987, pp. 1096–1097.

Gayed et al., "An Advanced Control Micromanipulator for Surgical Applications," *Systems Science* vol. 13, 1987, pp. 23–34.

Green et al., Abstract No. 704 of a presentation "Telepresence: Advanced Teleoperator Technology for Minimally Invasive Surgery," given at the 3rd World Congress of Endoscopic Surgery in Bordeaux, Jun. 18–20, 1992—"Session CL25/5" (2 pages total).

Green et al., Abstract of a presentation "Telepresence: Advanced Teleoperator Technology for Minimally Invasive Surgery," given at "Medicine Meets Virtual Reality: Discovering Applications for 3–D Multi–Media Interactive Technology in the Health Sciences" Symposium in San Diego, Jun. 4–7, 1992 (20 pages total).

Green, Statutory Declaration of Dr. Philip S. Green, presenter of the video entitled "Telepresence Surgery—The Future of Minimally Invasive Medicine," signed on Sep. 12, 2000, and filed with the European Patent Convention in the matter of EP–B–653–922 (32 pp).

Guerrouad et al., "S.M.O.S.: Stereotaxical Microtelemanipulator for Ocular Surgery," IEEE, 1989, pp. 879–880.

Inque et al., "Six–axis Bilateral Control of an Articulated Slave Manipulator Using a Cartesian Master Manipulator," Advanced Robotics, 4, No. 2, 1990, pp. 139–150.

Kazerooni, "Human/Robot Interaction via the Transfer of Power and Information Signals—Part I: Dynamics and Control Analysis," IEEE, 1989, pp. 1632–1640.

Kazerooni, "Human/Robot Interaction via the Transfer of Power and Information Signals—Part II: An Experimental Analysis," IEEE, 1989, pp. 1641–1647.

Krishnan et al., Abstract No. 276 of a presentation "Design Considerations of a New Generation Endoscopic Using Robotics and Computer Vision Technology," (session CL25/2) given at the 3rd World Congress of Endoscopic Surgery In Bordeaux, Jun. 18–20, 1992 (1 page total).

Lavallee, "A New System for Computer Assisted Neurosurgery," *IEEE Eng. in Med. & Biol. Soc.* 11th Annual International Conference, Jun. 1989, vol. 11, pp. 926–927.

Mair, Industrial Robotics, Prentice Hall, 1988, pp. 41–43, 49–50, 54, 203–209.

Majima et al., "On a Micro–Manipulator for Medical Application—Stability Consideration of its Bilateral Controller," Mechatronics, 1991, pp. 293–309.

NASA, "Anthropomorphic Remote Manipulator", NASA Tech. Briefs, 1991 (1 page total).

Preising et al., "A Literature Review: Robots in Medicine," IEEE, Jun. 1991, pp. 13–22 & 71.

Sabatini et al., "Force Feedback–Based Telemicromanipulation for Robot Surgery on Soft Tissues," IEEE, 1989, pp. 890–891.

Taubes, "Surgery in Cyberspace," Discovery Magazine, Dec. 1994, pp. 85–92.

Taylor et al., "Taming the Bull: Safety in a Precise Surgical Robot," IEEE, 1991, pp. 865–871.

Tejima, "A New Microsurgical Robot System for Corneal Transplantation," Precision Machinery, 1988 vol. 2, pp. 1–9.

Tendick et al., "Analysis of the Surgeon's Grasp for Telerobotic Surgical Manipulation," IEEE, 1989, pp. 914–915.

Thring, "*Robots and Telechirs*: Manipulator with Memory: Remote Manipulators: Machine Limbs for the Handicapped," John Wiley & Sons, 1983 (26 pages total).

Transcript of a video presented by SRI at the 3rd World Congress of Endoscopic Surgery in Bordeaux on Jun. 18–20, 1992, in Washington on Apr. 9, 1992, and in San Diego, CA on Jun. 4–7, 1992 entitled "Telepresence Surgery—The Future of Minimally Invasive Medicine" (3 pages total).

Trevelyan et al., "Motion Control for a Sheep Shearing Robot," Proceedings of the 1st International Symposium on Robotics Research, MIT, Cambridge, Massachusetts, USA, 1983, pp. 175.

Vibet, "Properties of Master–Slave Robots," Motor–con, 1987, pp. 309–314.

Video presented by SRI at the 3rd World Congress of Endoscopic Surgery in Bordeaux on Jun. 18–20, 1992, in Washington on Apr. 9, 1992, and in San Diego, CA on Jun. 4–7, 1992 entitled "Telepresence Surgery—The Future of Minimally Invasive Medicine" (VHS Tape).

Wolf et al., "Student Reference Manual for Electronic Instrumentation Laboratories," Prentice Hall, New Jersey 1990, pp. 498 and 499.

Notice of Opposition—European Patent Office dated Sep. 14, 2000, pp. 1–27.

Summons to Attend Oral Proceedings Pursuant to Rule 71(1), EPC, mailed Mar. 13, 2002, for Patent No. EP 0653922 B (28 pgs. total).

Brief Communication, mailed Jun. 3, 2002, for EP Patent No. EP 0653922 B, including Affidavit by Alberic George T.W. Fiennes signed May 20, 2002 (E58) relating to Besant Abstract (E6) (listed above) and NASA presentation by Keith L. Doty, "Kinematic Analysis of the Arid Manipulator" given on Aug. 7, 1992, at the Univ. of Florida, Gainesville, FL (E59) (52 pgs.).

Minutes of the Oral Proceedings Before the Opposition Division of Jul. 24, 2002, for EP Application No. 93 919 884.2 (Patent No. EP 0653922 B) between Computer Motion, Inc. v. Intuitive Surgical, Inc.

* cited by examiner

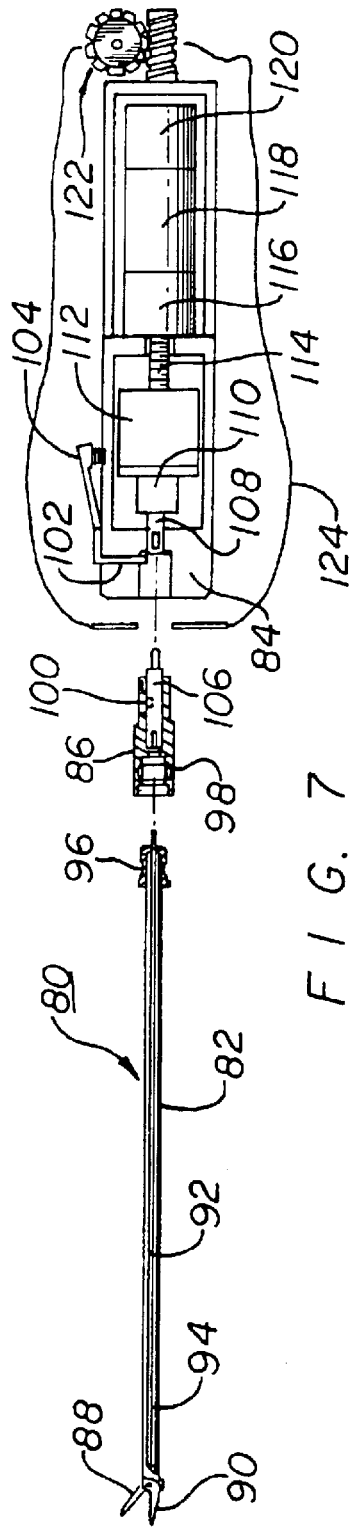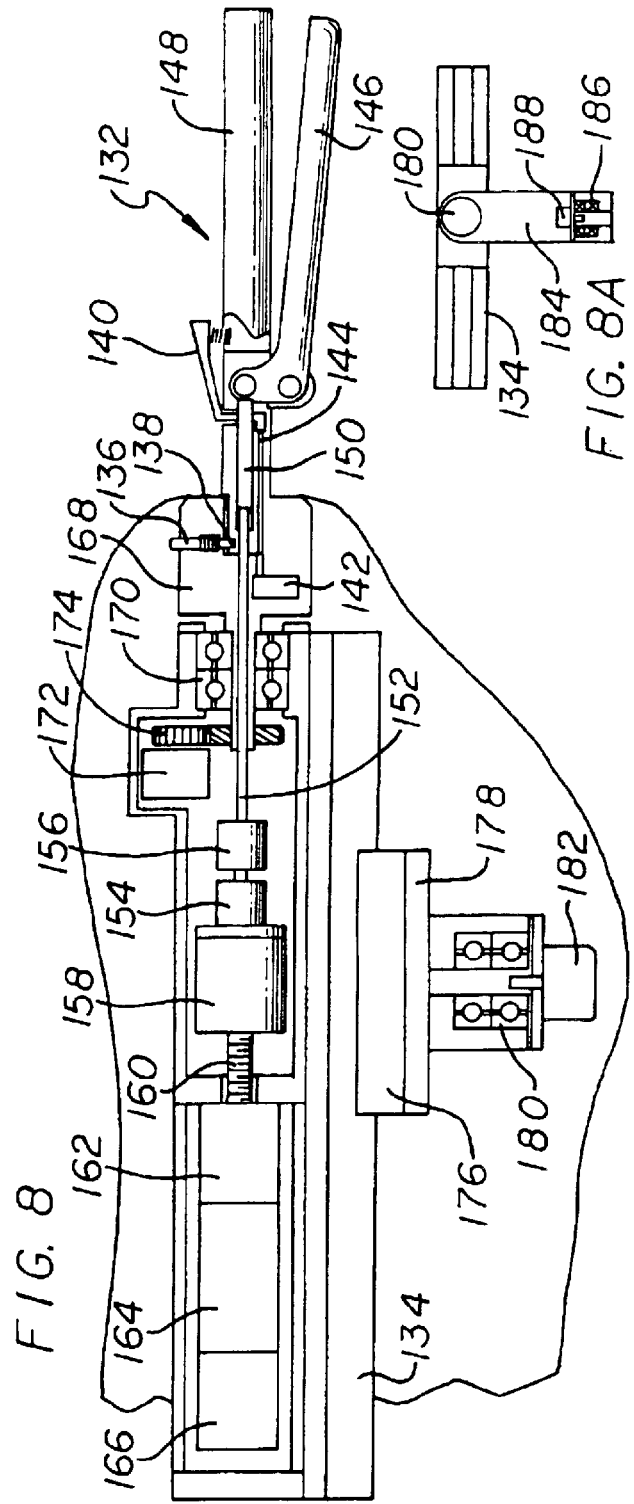

CORONARY ARTERY

INTERNAL MAMMARY ARTERY

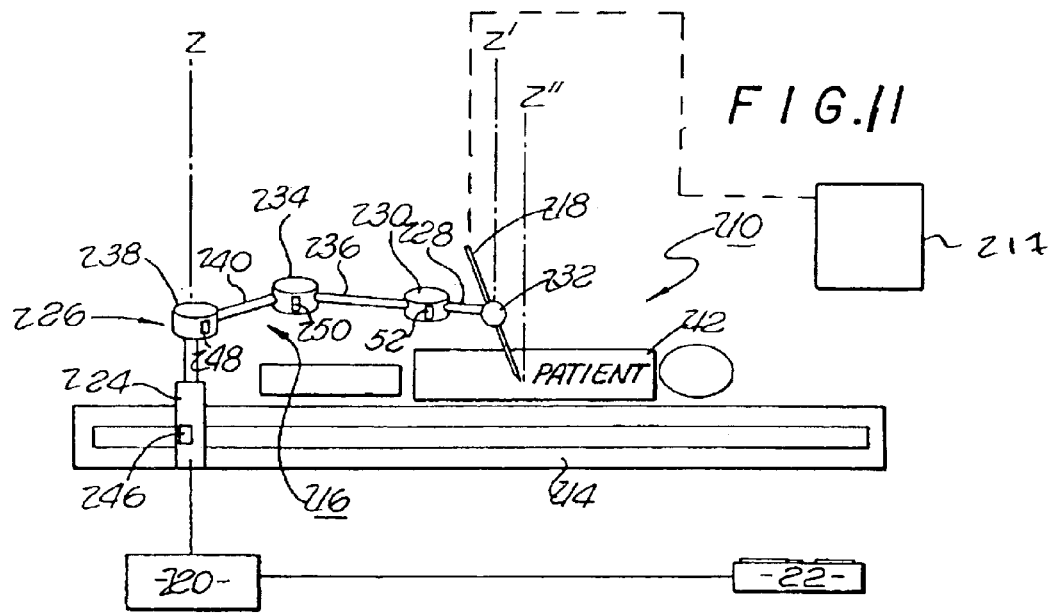
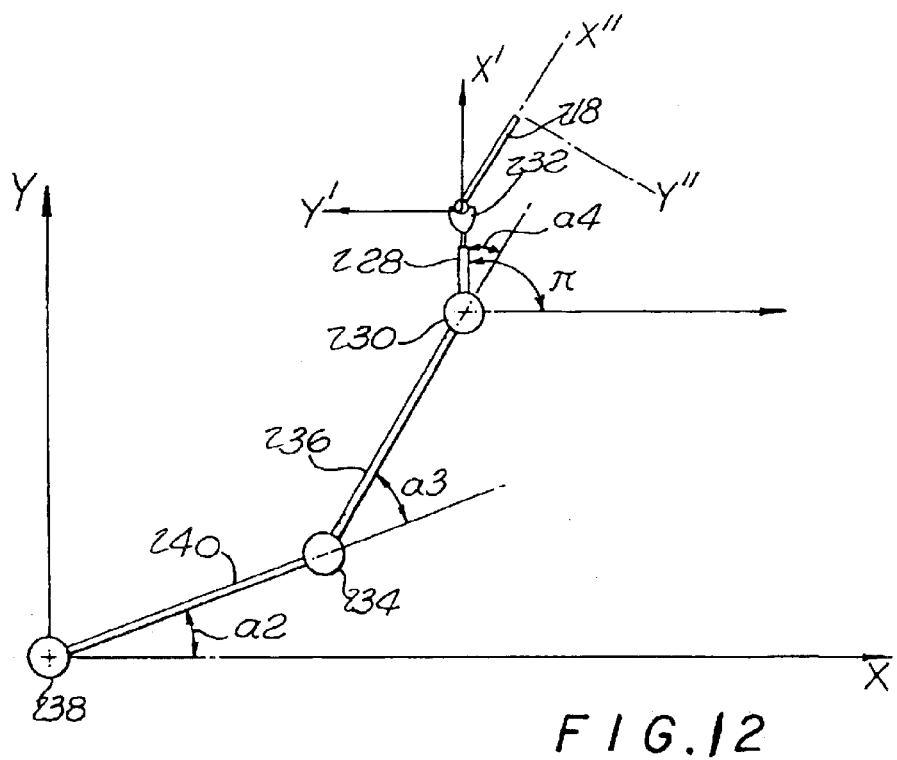
FIG.11
FIG.12

US 7,074,179 B2

METHOD AND APPARATUS FOR PERFORMING MINIMALLY INVASIVE CARDIAC PROCEDURES

REFERENCE TO CROSS-RELATED APPLICATIONS

This application is a continuation of application Ser. No. 09/000,934, filed on Dec. 30, 1997, now U.S. Pat. No. 6,905,491, which is a continuation-in-part of application Ser. No. 08/903,914, filed on Jul. 31, 1997, U.S. Pat. No. 5,815,640, which is a continuation of application Ser. No. 08/613,866, filed on Mar. 11, 1996, U.S. Pat. No. 5,907,664, which is a continuation of application Ser. No. 08/072,982, filed on Jun. 3, 1993, U.S. Pat. No. 5,524,180, which a continuation-in-part of application Ser. No. 08/005,604, filed on Jan. 19, 1993, abandoned, which is a continuation-in-part of application Ser. No.07/927,801, filed on Aug. 10, 1992, abandoned.

BACKGROUND OF THE INVENTION

1. Field of the Invention

The present invention relates to a system and method for performing minimally invasive cardiac procedures.

2. Description of Related Art

Blockage of a coronary artery may deprive the heart of the blood and oxygen required to sustain life. The blockage may be removed with medication or by an angioplasty. For severe blockage a coronary artery bypass graft (CABG) is performed to bypass the blocked area of the artery. CABG procedures are typically performed by splitting the sternum and pulling open the chest cavity to provide access to the heart. An incision is made in the artery adjacent to the blocked area. The internal mammary artery (IMA) is then severed and attached to the artery at the point of incision. The IMA bypasses the blocked area of the artery to again provide a full flow of blood to the heart. Splitting the sternum and opening the chest cavity can create a tremendous trauma on the patient. Additionally, the cracked sternum prolongs the recovery period of the patient.

There have been attempts to perform CABG procedures without opening the chest cavity. Minimally invasive procedures are conducted by inserting surgical instruments and an endoscope through small incision in the skin of the patient. Manipulating such instruments can be awkward, particularly when suturing a graft to a artery. It has been found that a high level of dexterity is required to accurately control the instruments. Additionally, human hands typically have at least a minimal amount of tremor. The tremor further increases the difficulty of performing minimal invasive cardiac procedures. It would be desirable to provide a system for effectively performing minimally invasive coronary artery bypass graft procedures.

BRIEF SUMMARY OF THE INVENTION

The present invention is a system for performing minimally invasive cardiac procedures. The system includes a pair of surgical instruments that are coupled to a pair of robotic arms. The instruments have end effectors that can be manipulated to hold and suture tissue. The robotic arms are coupled to a pair of master handles by a controller. The handles can be moved by the surgeon to produce a corresponding movement of the end effectors. The movement of the handles is scaled so that the end effectors have a corresponding movement that is different, typically smaller, than the movement performed by the hands of the surgeon. The scale factor is adjustable so that the surgeon can control the resolution of the end effector movement. The movement of the end effector can be controlled by an input button, so that the end effector only moves when the button is depressed by the surgeon. The input button allows the surgeon to adjust the position of the handles without moving the end effector, so that the handles can be moved to a more comfortable position. The system may also have a robotically controlled endoscope which allows the surgeon to remotely view the surgical site. A cardiac procedure can be performed by making small incisions in the patient's skin and inserting the instruments and endoscope into the patient. The surgeon manipulates the handles and moves the end effectors to perform a cardiac procedure such as a coronary artery bypass graft.

BRIEF DESCRIPTION OF THE DRAWINGS

The objects and advantages of the present invention will become more readily apparent to those ordinarily skilled in the art after reviewing the following detailed description and accompanying drawings, wherein:

FIG. 7 is an exploded view of an end effector of the system;

FIG. 8 is a top view of a master handle of the system;

FIG. 8a is a side view of the master handle;

FIG. 11 is a side view of a robotic system of the present invention;

FIG. 12 is a top view of the robotic system of FIG. 11;

DETAILED DESCRIPTION OF THE INVENTION

Figure 1:
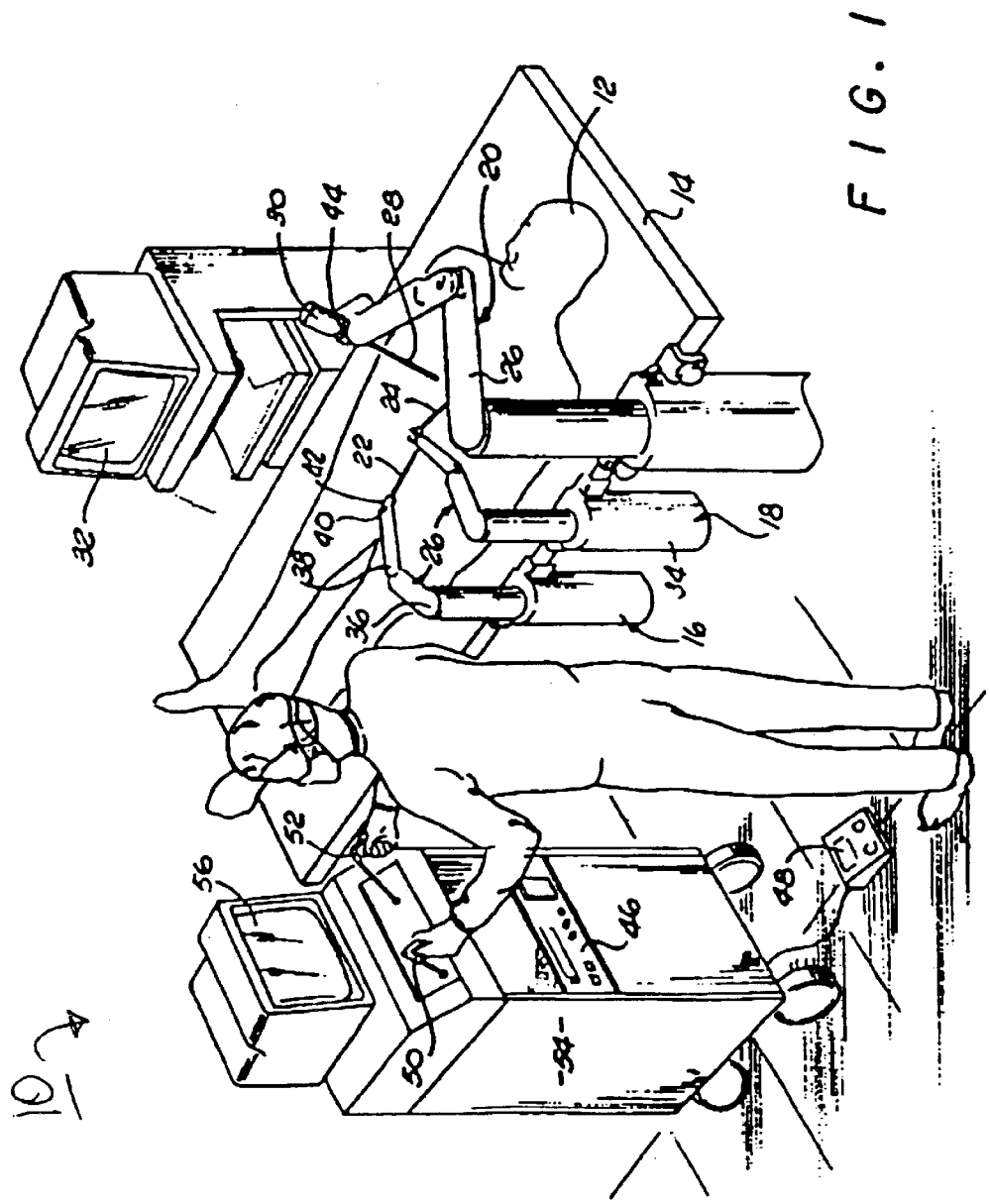
FIG. 1 is a perspective view of a minimally invasive surgical system of the present invention.

Referring to the drawings more particularly by reference numbers, FIG. 1 shows a system 10 that can perform minimally invasive surgery. In the preferred embodiment, the system 10 is used to perform a minimally invasive coronary artery bypass graft (MI-CABG) and other anastomostic procedures. Although a MI-CABG procedure is shown and described, it is to be understood that the system may be used for other surgical procedures. For example, the system can be used to suture any pair of vessels.

The system 10 is used to perform a procedure on a patient 12 that is typically lying on an operating table 14. Mounted to the operating table 14 is a first articulate arm 16, a second articulate arm 18 and a third articulate arm 20. The articulate arms 16, 18, 20 are preferably mounted to the table so that the arms are at a same reference plane as the patient. Although three articulate arms are shown and described, it is to be understood that the system may have any number of arms.

The first and second articulate arms 16 and 18 each have a surgical instrument 22 and 24 coupled to a robotic arm 26. The third articulate arm 20 has an endoscope 28 that is held by a robotic arm 26. The instruments 22 and 24, and endoscope 28 are inserted through incisions cut into the skin of the patient. The endoscope has a camera 30 that is coupled to a television monitor 32 which displays images of the internal organs of the patient.

The robotic arms 26 each have a linear motor 34, a first rotary motor 36 and a second rotary motor 38. The robotic arms 26 also have a pair of passive joints 40 and 42. The articulate arm 20 also have a worm gear 44 and means to couple the instruments 22 and 24, and endoscope 28 to the robotic arm 26. The first, second, and third articulate arms are coupled to a controller 46 which can control the movement of the arms.

The controller 46 is connected to an input device 48 such as a foot pedal that can be operated by a surgeon to move the location of the endoscope and view a different portion of the patient by depressing a corresponding button(s) of the foot pedal 48. The controller 46 receives the input signals from the foot pedal 48 and moves the robotic arm 26 and endoscope 28 in accordance with the input commands of the surgeon. The robotic arms may be devices that are sold by the assignee of the present invention. Computer Motion, Inc. of Goleta, Calif., under the trademark AESOP. The system is also described in allowed U.S. application Ser. No. 08/305,415, now U.S. Pat. No. 5,515,478, which is hereby incorporated by reference. Although a foot pedal 48 is shown and described, it is to be understood that the system may have other input means such as a hand controller, or a speech recognition interface.

The instruments 22 of the first 16 and second 18 articulate arms are controlled by a pair of master handles 50 and 52 that can be manipulated by the surgeon. The handles 50 and 52, and arms 16 and 18, have a master-slave relationship so that movement of the handles produces a corresponding movement of the surgical instruments. The handles 50 and 52 may be mounted to a portable cabinet 54. A second television monitor 56 may be placed onto the cabinet 54 and coupled to the endoscope 28 so that the surgeon can readily view the internal organs of the patient. The handles 50 and 52 are also coupled to the controller 46. The controller 46 receives input signals from the handles 50 and 52, computes a corresponding movement of the surgical instruments, and provides output signals to move the robotic arms and instruments.

Figure 2:
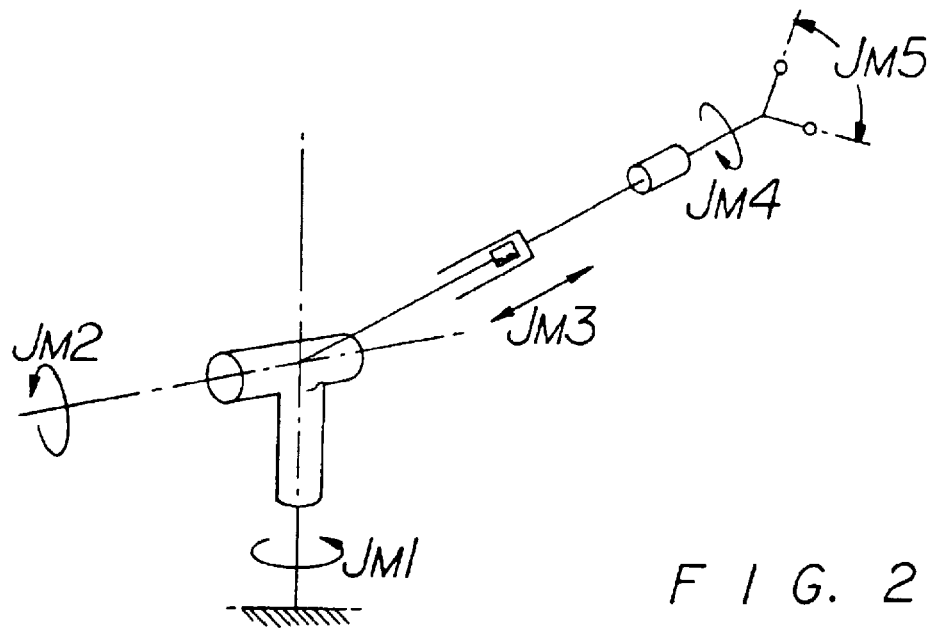
FIG. 2 is a schematic of a master of the system.

Each handle has multiple degrees of freedom provided by the various joints $Jm1$–$Jm5$ depicted in FIG. 2. Joints $Jm1$ and $Jm2$ allow the handle to rotate about a pivot point of the cabinet 54. Joint $Jm3$ allows the surgeon to move the handle into and out of the cabinet 54 in a linear manner. Joint $Jm4$ allows the surgeon to rotate the master handle about a longitudinal axis of the handle. The joint $Jm5$ allows a surgeon to open and close a gripper. Each joint $Jm1$–$Jm5$ has a position sensor which provides feedback signals that correspond to the relative position of the handle. The position sensors may be potentiometers, or any other feedback device, that provides an electrical signal which corresponds to a change of position.

Figure 3:
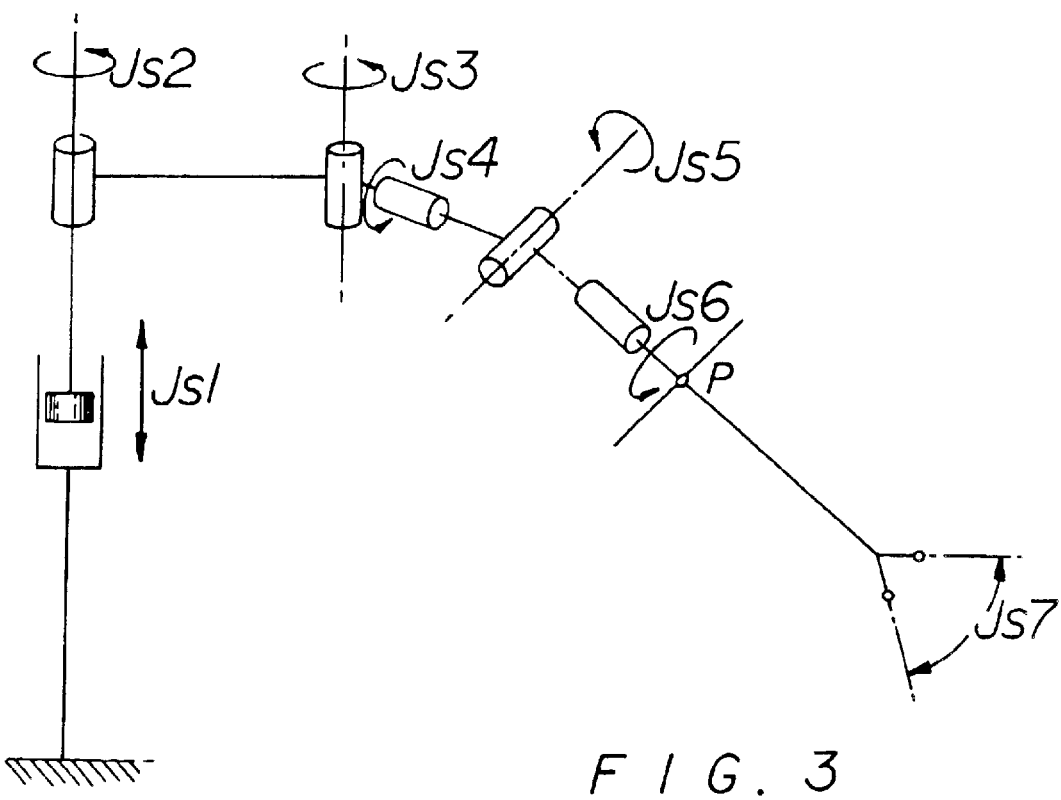
FIG. 3 is a schematic of a slave of the system.

FIG. 3 shows the various degrees of freedom of each articulate arm 16 and 18. The joints $Js1$, $Js2$ and $Js3$ correspond to the linear motor and rotary motors of the robotic arms 26, respectively. The joints $Js4$ and $Js5$ correspond to the passive joints 40 and 42 of the arms 26. The joint $Js6$ may be a motor which rotates the surgical instruments about the longitudinal axis of the instrument. The joint $Js7$ may be a pair of fingers that can open and close. The instruments 22 and 24 move about a pivot point P located at the incision of the patient.

Figure 4:
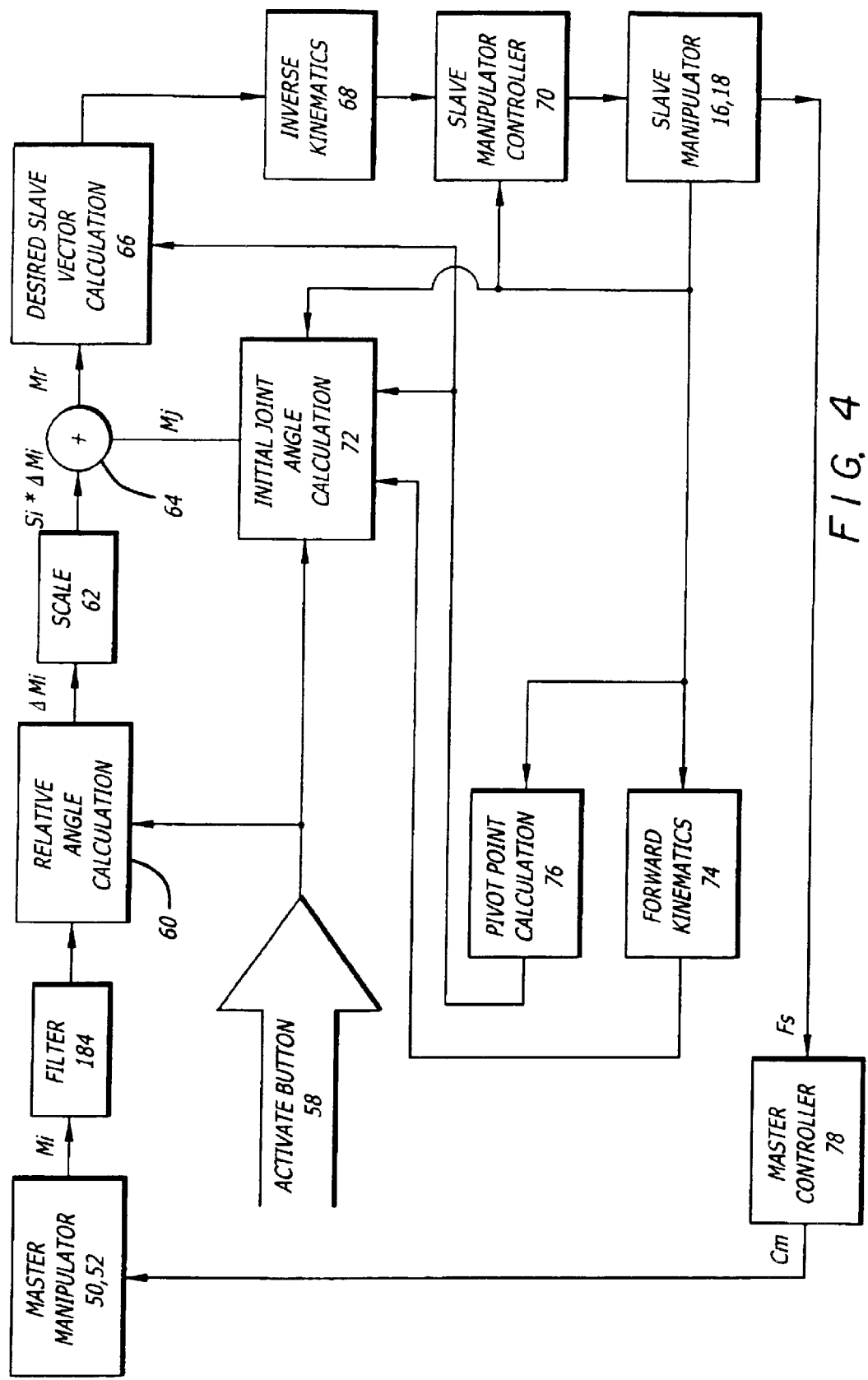
FIG. 4 is a schematic of a control system of the system.

FIG. 4 shows a schematic of a control system that translates a movement of a master handle into a corresponding movement of a surgical instrument. In accordance with the control system shown in FIG. 4, the controller 46 computes output signals for the articulate arms so that the surgical instrument moves in conjunction with the movement of the handle. Each handle may have an input button 58 which enables the instrument to move with the handle. When the input button 58 is depressed the surgical instrument follows the movement of the handle. When the button 58 is released the instrument does not track the movement of the handle. In this manner the surgeon can adjust or "ratchet" the position of the handle without creating a corresponding undesirable movement of the instrument. The "ratchet" feature allows the surgeon to continuously move the handles to more desirable positions without altering the positions of the arms. Additionally, because the handles are constrained by a pivot point the ratchet feature allows the surgeon to move the instruments beyond the dimensional limitations of the handles. Although an input button is shown and described, it is to be understood that the surgical instrument may be activated by other means such as voice recognition. The input button may be latched so that activation of the instrument toggles between active and inactive each time the button is depressed by the surgeon.

When the surgeon moves a handle, the position sensors provide feedback signals $M1$–$M5$ that correspond to the movement of the joints $Jm1$–$Jm5$, respectively. The controller 46 computes the difference between the new handle position and the original handle position in computation block 60 to generate incremental position values $\Delta M1$–$\Delta M5$.

The incremental position values $\Delta M1$–$\Delta M5$ are multiplied by scale factors $S1$–$S5$, respectively in block 62. The scale factors are typically set at less than one so that the movement of the instrument is less than the movement of the handle. In this manner the surgeon can produce very fine movements of the instruments with relatively coarse movements of the handles. The scale factors $S1$–$S5$ are variable so that the surgeon can vary the resolution of instrument movement. Each scale factor is preferably individually variable so that the surgeon can more finely control the instrument in certain directions. By way of example, by setting one of the scale factors at zero the surgeon can prevent the instrument from moving in one direction. This may be advantageous if the surgeon does not want the surgical instrument to contact an organ or certain tissue located in a certain direction relative to the patient. Although scale factors smaller than a unit one described, it is to be understood that a scale factor may be greater than one. For example, it may be desirable to spin the instrument at a greater rate than a corresponding spin of the handle.

The controller 46 adds the incremental values $\Delta M1$–$\Delta M5$ to the initial joint angles $Mj1$–$Mj5$ in adder element 64 to provide values Mr1–Mr5. The controller 46 then computes desired slave vector calculations in computation block 66 in accordance with the following equations.

$$Rdx=Mr3\cdot\sin(Mr1)\cdot\cos(Mr2)+Px$$

$$Rdy=Mr1\cdot\sin(Mr1)\cdot\sin(Mr2)+Py$$

$$Rdz=Mr3\cdot\cos(Mr1)+Pz$$

$$Sdr=Mr4$$

$$Sdg=Mr5$$

where;
Rdx, y, z=the new desired position of the end effector of the instrument.
Sdr=the angular rotation of the instrument about the instrument longitudinal axis.
Sdg=the amount of movement of the instrument fingers.
Px, y, z=the position of the pivot point P.

The controller 46 then computes the movement of the robotic arm 26 in computational block 68 in accordance with the following equations.

$$Jsd1=Rdz$$

$$Jsd3 = p - \cos^{-1}\left[\frac{Rdx^2 + Rdy^2 - L1^2 - L2^2}{2L1 \times L2}\right]$$

$$Jsd2=\tan^{-1}(Rdy/Rdx)=D \text{ for } Jsd3 \pounds 0$$

$$Jsd2=\tan^{-1}(Rdy/Rdx)-D \text{ for } Jsd3>0$$

$$D = \cos^{-1}\left[\frac{Rdx^2 + Rdy^2 - L1^2 - L2^2}{2 \times L1\sqrt{Rdx^2 + Rdy^2}}\right]$$

$$Jsd6=Mr4$$

$$Jsd7=Mr5$$

where;
Jsd1=the movement of the linear motor.
Jsd2=the movement of the first rotary motor.
Jsd3=the movement of the second rotary motor.
Jsd6=the movement of the rotational motor.
Jsd7=the movement of the gripper.
L1=the length of the linkage arm between the first rotary motor and the second rotary motor.
L2=the length of the linkage arm between the second rotary motor and the passive joints.

The controller provides output signals to the motors to move the arm and instrument in the desired location in block 70. This process is repeated for each movement of the handle.

The master handle will have a different spatial position relative to the surgical instrument if the surgeon releases the input button and moves the handle. When the input button 58 is initially depressed, the controller 46 computes initial joint angles Mj1–Mj5 in computational block 72 with the following equations.

$$Mj1=\tan^{-1}(ty/tx)$$

$$Mj2=\tan^{-1}(d/tz)$$

$$Mj3=D$$

$$Mj4=Js6$$

$$Mj5=Js7$$

$$d=\sqrt{tx^2+ty^2}$$

$$tx = \frac{Rsx - Px}{D} \quad ty = \frac{Rsy - Py}{D} \quad tz = \frac{Rsz - Pz}{D}$$

$$D = \sqrt{(Rsx - Px)^2 + (Rsy - Py)^2 + (Rsz - Pz)^2}$$

The forward kinematic values are computed in block 74 with the following equations.

$$Rsx=L1\cdot\cos(Js2)+L2\cdot\cos(Js2+Js3)$$

$$Rsy=L1\cdot\cos(Js2)-L2\cdot\sin(Js2+Js3)$$

$$Rsz=J1$$

Figure 5:
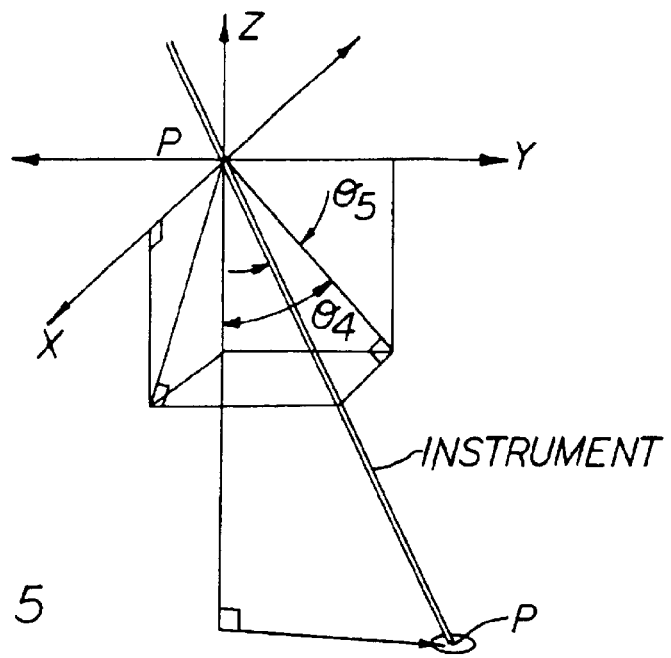
FIG. 5 is a schematic showing the instrument in a coordinate frame.

The joint angles Mj are provided to adder 64. The pivot points Px, Py and Pz are computed in computational block 76 as follows. The pivot point is calculated by initially determining the original position of the intersection of the end effector and the instrument PO, and the unit vector Uo which has the same orientation as the instrument. The position P(x, y, z) values can be derived from various position sensors of the robotic arm. Referring to FIG. 5 the instrument is within a first coordinate frame (x, y, z) which has the angles θ4 and θ5. The unit vector Uo is computed by the transformation matrix:

$$Uo = \begin{bmatrix} \cos\Theta_5 & 0 & -\sin\Theta_5 \\ -\sin\Theta_4\sin\Theta_5 & \cos\Theta_4 & -\sin\Theta_4\cos\Theta_5 \\ \cos\Theta_4\sin\Theta_5 & \sin\Theta_4 & \cos\Theta_4 \end{bmatrix} \begin{bmatrix} 0 \\ 0 \\ -1 \end{bmatrix}$$

After each movement of the end effector an angular movement of the instrument Δθ is computed by taking the arcsin of the cross-product of the first and second unit vectors Uo and U1 of the instrument in accordance with the following line equations Lo and L1.

$$\Delta\theta=\arcsin(|T|)$$

$$T=Uo\times U1$$

where;
T=a vector which is a cross-product of unit vectors Uo and U1.

Figure 6:
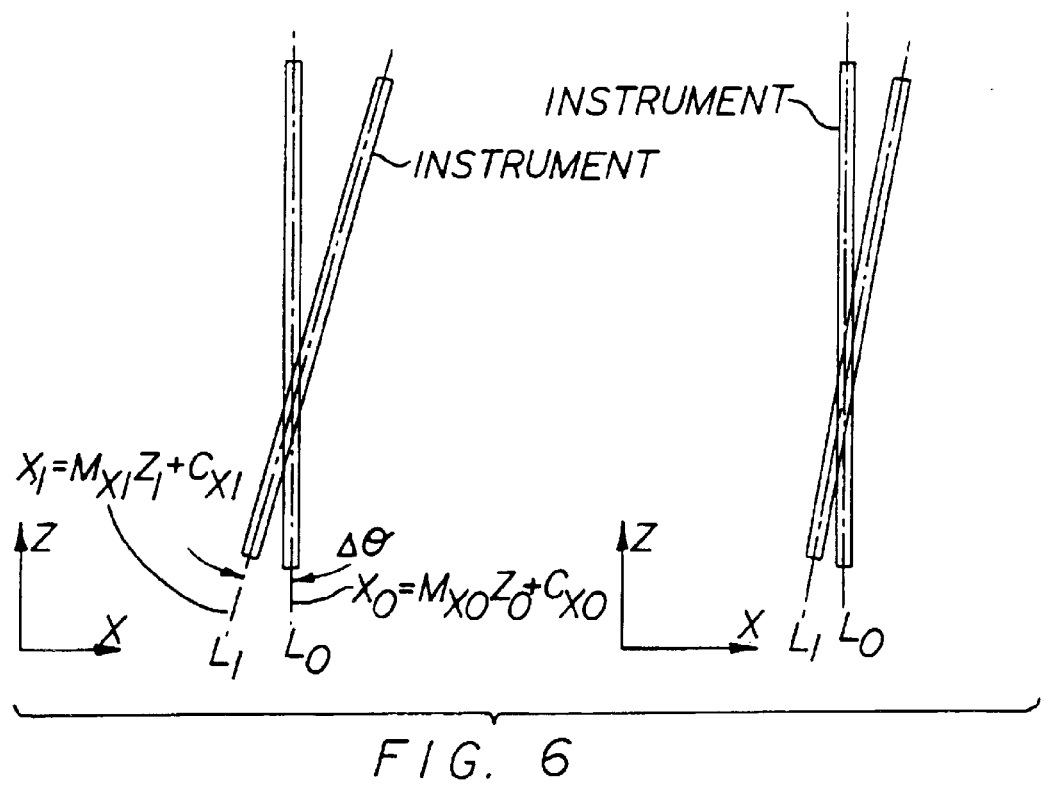
FIG. 6 is a schematic of the instrument moving about a pivot point.
Figure 9:
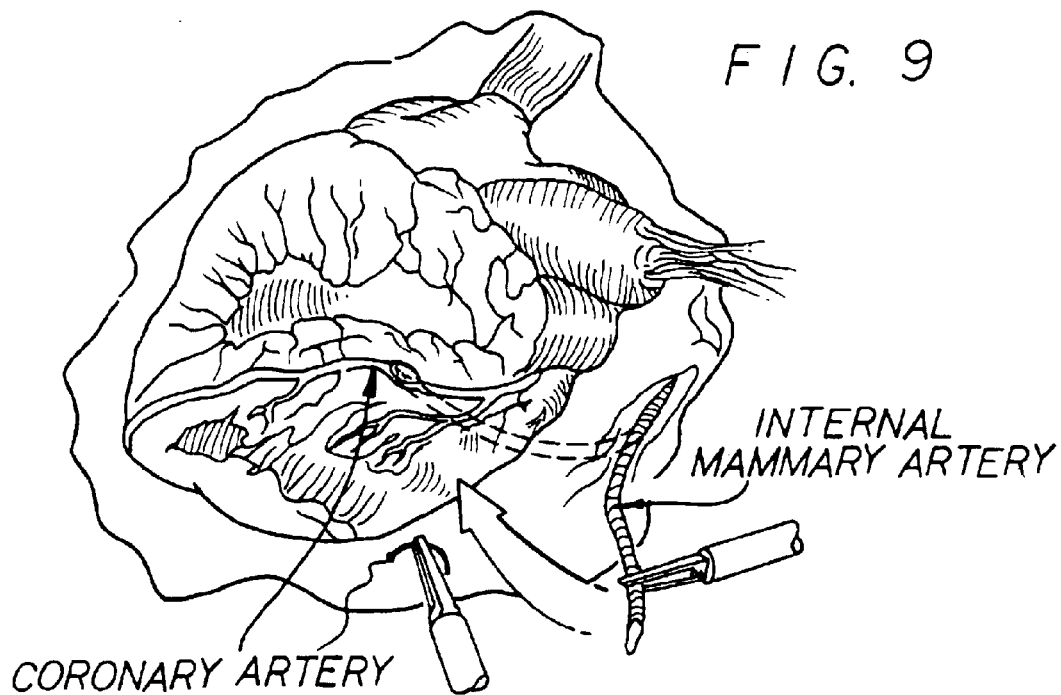
FIGS. 9–10A–I are illustrations showing an internal mammary artery being grafted to a coronary artery.

The unit vector of the new instrument position U1 is again determined using the positions sensors and the transformation matrix described above. If the angle Δθ is greater than a threshold value, then a new pivot point is calculated and Uo is set to U1. As shown in FIG. 6, the first and second instrument orientations can be defined by the line equations Lo and L1:

Lo:

$$xo=Mxo\cdot Zo+Cxo$$

$$yo=Myo\cdot Zo+Cyo$$

L1

$$x1=Mx1\cdot Z1=Cx1$$

$$y1=My1\cdot Z1+Cy1$$

where;

Zo=a Z coordinate along the line Lo relative to the z axis of the first coordinate system.

Z1=a Z coordinate along the line L1 relative to the z axis of the first coordinate system.

Mxo=a slope of the line Lo as a function of Zo.

Myo=a slope of the line Lo as a function of Zo.

Mx1=a slope of the line L1 as a function of Z1.

My1=a slope of the line L1 as a function of Z1.

Cxo=a constant which represents the intersection of the line Lo and the x axis of the first coordinate system.

Cyo=a constant which represents the intersection of the line Lo and the y axis of the first coordinate system.

Cx1=a constant which represents the intersection of the L1 and the x axis of the first coordinate system.

Cy1=a constant which represents the intersection of the line L1 and the y axis of the first coordinate system.

The slopes are computed using the following algorithms:

$$Mxo = Uxo/Uzo$$

$$Myo = Uyo/Uzo$$

$$Mx1 = Ux1/Uzi$$

$$My1 = Uy1/Uz1$$

$$Cx0 = Pox - Mx1 \cdot Poz$$

$$Cy0 = Poy - My1 \cdot Poz$$

$$Cx1 = P1x - Mx1 \cdot P1z$$

$$Cy1 = P1y - My1 \cdot P1z$$

where;

Uo (x, y and z)=the unit vectors of the instrument in the first position within the first coordinate system.

U1 (x, y and z)=the unit vectors of the instrument in the second position within the first coordinate system.

Po (x, y and z)=the coordinates of the intersection of the end effector and the instrument in the first position within the first coordinate system.

P1 (x, y and z)=the coordinates of the intersection of the end effector and the instrument in the second position within the first coordinate system.

To find an approximate pivot point location, the pivot points of the instrument in the first orientation Lo (pivot point Ro) and in the second orientation L1 (pivot point R1) are determined, and the distance half way between the two points Ro and R1 is computed and stored as the pivot point $R_{ave}$ of the instrument. The pivot point $R_{ave}$ is determined by using the cross-product vector T.

To find the points Ro and R1 the following equalities are set to define a line with the same orientation as the vector T that passes through both Lo and L1.

$$tx = Tx/Tz$$

$$ty = Ty/Tz$$

where;

tx=the slope of a line defined by vector T relative to the Z–x plane of the first coordinate system.

ty=the slope of a line defined by vector T relative to the Z–y plane of the first coordinate system.

Tx=the x component of the vector T.

Ty=the y component of the vector T.

Tz=the z component of the vector T.

Picking two points to determine the slopes Tx, Ty and Tz (e.g. Tx=x1−xo, Ty=y1−yo and Tz=z1−z0) and substituting the line equations Lo and L1, provides a solution for the point coordinates for Ro (xo, yo, zo) and R1 (xl, yl, zl) as follows.

$$zo = ((Mx1-tx)z1 + Cx1 - Cxo)/(Mxo-tx)$$

$$z1 = ((Cy1-Cyo)(Mxo-tx) - (Cx1-Cxo)(Myo-ty))/((Myo-ty)(Mx1-tx) - (My1-ty)(Mxo-tx))$$

$$yo = Myo \cdot zo + Cyo$$

$$y1 = My1 \cdot z1 + Cy1$$

$$xo = Mxo \cdot zo + Cxo$$

$$x1 = Mx1 \cdot z1 + Cx1$$

The average distance between the pivot points Ro and R1 is computed with the following equation and stored as the pivot point of the instrument.

$$R_{ave} = ((x1+xo)/2, (y1+yo)/2, (z1+zo)/2)$$

The pivot point can be continually updated with the above described algorithm routine. Any movement of the pivot point can be compared to a threshold value and a warning signal can be issued or the robotic system can become disengaged if the pivot point moves beyond a set limit. The comparison with a set limit may be useful in determining whether the patient is being moved, or the instrument is being manipulated outside of the patient, situations which may result in injury to the patient or the occupants of the operating room.

To provide feedback to the surgeon the fingers of the instruments may have pressure sensors that sense the reacting force provided by the object being grasped by the end effector. Referring to FIG. 4, the controller 46 receives the pressure sensor signals Fs and generates corresponding signals Cm in block 78 that are provided to an actuator located within the handle. The actuator provides a corresponding pressure on the handle which is transmitted to the surgeon's hand. The pressure feedback allows the surgeon to sense the pressure being applied by the instrument. As an alternate embodiment, the handle may be coupled to the end effector fingers by a mechanical cable that directly transfers the grasping force of the fingers to the hands of the surgeon.

FIG. 7 shows a preferred embodiment of an end effector 80. The end effector 80 includes a tool 82 that is coupled to an arm 84 by a sterile coupler 86. The tool 82 has a first finger 88 that is pivotally connected to a second finger 90. The fingers can be manipulated to hold objects such as tissue or a suturing needle. The inner surface of the fingers may have a texture to increase the friction and grasping ability of the tool. The first finger 88 is coupled to a rod 92 that extends through a center channel 94 of the tool 82. The tool 82 may have an outer sleeve 96 which cooperates with a spring biased ball quick disconnect fastener 98 of the sterile coupler 86. The quick disconnect allows tools other than the finger grasper to be coupled to an arm. For example, the tool 82 may be decoupled from the coupler and replaced by a cutting tool. The coupler 86 allows the surgical instruments to be interchanged without having to re-sterilize the arm each time an instrument is plugged into the arm.

The sterile coupler 86 has a slot 100 that receives a pin 102 of the arm 84. The pin 102 locks the coupler 86 to the arm 84. The pin 102 can be released by depressing a spring biased lever 104. The sterile coupler 86 has a piston 106 that is attached to the tool rod and in abutment with an output piston 108 of a load cell 110 located within the arm 84.

The load cell 110 is mounted to a lead screw nut 112. The lead screw nut 112 is coupled to a lead screw 114 that extends from a gear box 116. The gear box 116 is driven by a reversible motor 118 that is coupled to an encoder 120. The entire arm 82 is rotated by a motor drive worm gear 122. In operation, the motor receives input commands from the controller 46 and activates, accordingly. The motor 118 rotates the lead screw 114 which moves the lead screw nut 112 and load cell 110 in a linear manner. Movement of the load cell 110 drives the coupler piston 106 and tool rod 92, which rotate the first finger 88. The load cell 110 senses the counteractive force being applied to the fingers and provides a corresponding feedback signal to the controller 46. The arm 84 may be covered with a sterile drape 124 so that the arm does not have to be sterilized after each surgical procedure.

FIGS. 8 and 8*a* show a preferred embodiment of a master handle assembly 130. The assembly 130 includes a master handle 132 that is coupled to an arm 134. The master handle 132 may be coupled to the arm 134 by a pin 136 that is inserted into a corresponding slot 138 in the handle 132. The handle 132 has a control button 140 that can be depressed by the surgeon. The control button 140 is coupled to a switch 142 by a shaft 144. The control button 140 corresponds to the input button 58 shown in FIG. 4, and activates the movement of the end effector.

The master handle 132 has a first gripper 146 that is pivotally connected to a second stationary gripper 148. Rotation of the first gripper 146 creates a corresponding linear movement of a handle shaft 150. The handle shaft 150 moves a gripper shaft 152 that is coupled to a load cell 154 by a bearing 156. The load cell 154 senses the amount of pressure being applied thereto and provides an input signal to the controller 46. The controller 46 then provides an output signal to move the fingers of the end effector.

The load cell 154 is mounted to a lead screw nut 158 that is coupled to a lead screw 160. The lead screw 160 extends from a reduction box 162 that is coupled to a motor 164 which has an encoder 166. The controller 46 of the system receives the feedback signal of the load cell 110 in the end effector and provides a corresponding command signal to the motor to move the lead screw 160 and apply a pressure on the gripper so that the surgeon receives feedback relating to the force being applied by the end effector. In this manner the surgeon has a "feel" for operating the end effector.

The handle is attached to a swivel housing 168 that rotates about bearing 170. The swivel housing 168 is coupled to a position sensor 172 by a gear assembly 174. The position sensor 172 may be a potentiometer which provides feedback signals to the controller 46 that correspond to the relative position of the handle. The swivel movement is translated to a corresponding spin of the end effector by the controller and robotic arm.

The arm 134 may be coupled to a linear bearing 176 and corresponding position sensor 178 which allow and sense linear movement of the handle. The linear movement of the handle is translated into a corresponding linear movement of the end effector by the controller and robotic arm. The arm can pivot about bearings 180, and be sensed by position sensor 182 located in a stand 184. The stand 184 can rotate about bearing 186 which has a corresponding position sensor 188. The arm rotation is translated into corresponding pivot movement of the end effector by the controller and robotic arm.

A human hand will have a natural tremor typically resonating between 6–12 hertz. To eliminate tracking movement of the surgical instruments with the hand tremor, the system may have a filter that filters out any movement of the handles that occurs within the tremor frequency bandwidth. Referring to FIG. 4, the filter 184 may filter analog signals provided by the potentiometers in a frequency range between 6–12 hertz.

As shown in FIGS. 9 and 10A–I, the system is preferably used to perform a cardiac procedure such as a coronary artery bypass graft (CABG). The procedure is performed by initially cutting three incisions in the patient and inserting the surgical instruments 22 and 24, and the endoscope 26 through the incisions. One of the surgical instruments 22 holds a suturing needle and accompanying thread when inserted into the chest cavity of the patient. If the artery is to be grafted with a secondary vessel, such as a saphenous vein, the other surgical instrument 24 may hold the vein while the end effector of the instrument is inserted into the patient.

The internal mammary artery (IMA) may be severed and moved by one of the instruments to a graft location of the coronary artery. The coronary artery is severed to create an opening in the artery wall of a size that corresponds to the diameter of the IMA. The incision(s) may be performed by a cutting tool that is coupled to one of the end effectors and remotely manipulated through a master handle. The arteries are clamped to prevent a blood flow from the severed mammary and coronary arteries. The surgeon manipulates the handle to move the IMA adjacent to the opening of the coronary artery. Although grafting of the IMA is shown and described, it is to be understood that another vessel such as a severed saphaneous vein may be grafted to bypass a blockage in the coronary artery.

Figure 10A:
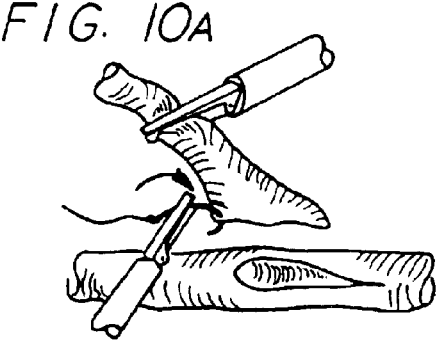
Figure 10B:
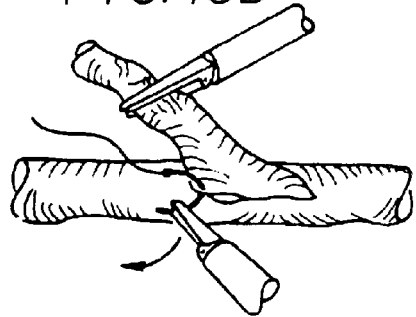
Figure 10C:
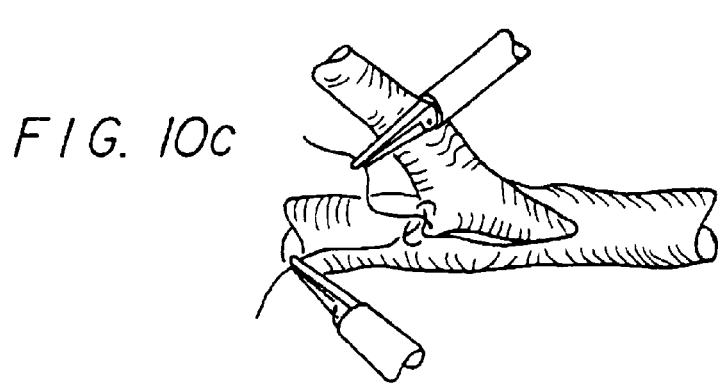
Figure 10D:
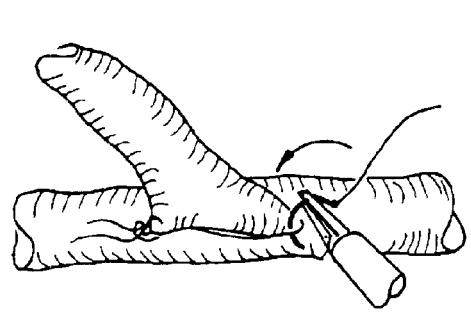
Figure 10E:
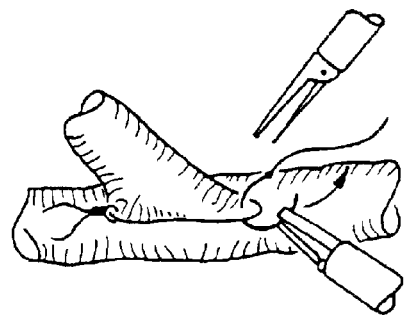
Figure 10F:
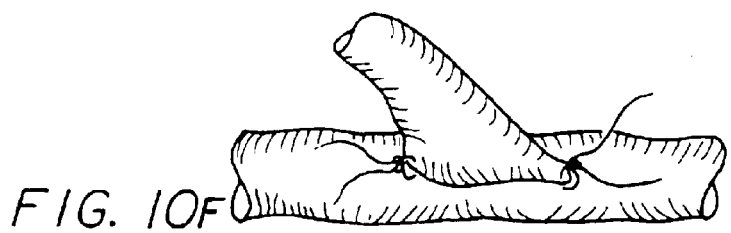
Figure 10G:
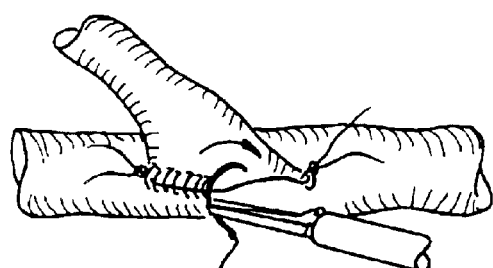
Figure 10H:
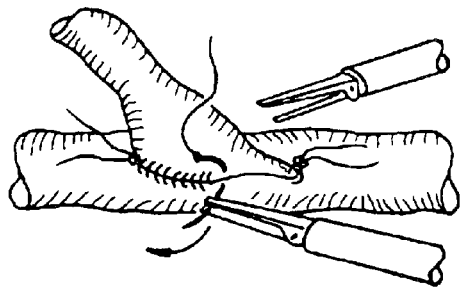
Figure 10I:
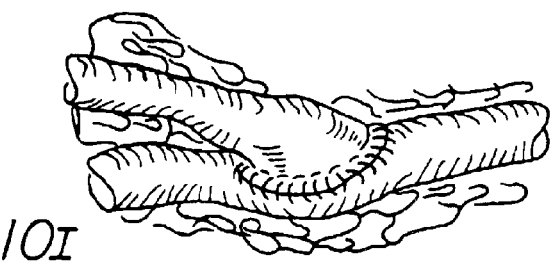

Referring to FIGS. 10A–I, the surgeon moves the handle to manipulate the instrument into driving the needle through the IMA and the coronary artery. The surgeon then moves the surgical instrument to grab and pull the needle through the coronary and graft artery as shown in FIG. 10B. As shown in FIG. 10C, the surgical instruments are then manipulated to tie a suture at the heel of the graft artery. The needle can then be removed from the chest cavity. As shown in FIGS. 10D–F, a new needle and thread can be inserted into the chest cavity to suture the toe of the graft artery to the coronary artery. As shown in FIG. 10H–J, new needles can be inserted and the surgeon manipulates the handles to create running sutures from the heel to the toe, and from the toe to the heel. The scaled motion of the surgical instrument allows the surgeon to accurately move the sutures about the chest cavity. Although a specific graft sequence has been shown and described, it is to be understood that the arteries can be grafted with other techniques. In general the system of the present invention may be used to perform any minimally invasive anastomostic procedure.

Referring to the drawings more particularly by reference numbers, FIGS. 11 and 12 show a robotic system 210 of the present invention. The system 210 is typically used in a sterile operating room where a surgeon (not shown) performs a surgical procedure on a patient 212. The patient 212 is placed on a operating table 214. Attached to the table 214 is a robotic arm assembly 216 which can move a surgical instrument 218 relative to the table 214 and the patient 212. The surgical instrument 218 is typically an endoscope which is inserted into the abdomen of the patient 212. The endoscope 18 enters the patient through cannula, wherein the scope 218 rotate about a cannula pivot point. The endoscope is typically connected to a display screen (not shown) which allows the surgeon to view the organs, etc. of the patient. Although an endoscope is described and shown, it is to be understood that the present invention can be used with other surgical instruments.

The system 210 has a computer 220 that is connected to the robotic arm assembly 216 and a foot pedal 222. The foot pedal 222 is located in close proximity to the operating table 214, so that the surgeon can operate the foot pedal 222 while performing a surgical procedure. The system 210 is constructed so that the surgeon can move the surgical instrument 218 by merely depressing the foot pedal 222.

The robotic arm assembly 216 includes a linear actuator 224 fixed to the table 214. The linear actuator 224 is connected to a linkage arm assembly 226 and adapted to move the linkage assembly 226 along the z axis of a first coordinate system. As shown in FIG. 12, the first coordinate system also has an x axis and a y axis. The linear actuator 224 preferably has an electric motor which turns a ball screw that moves the output shaft of the actuator.

The linkage arm assembly 226 includes a first linkage arm 228 attached to a first rotary actuator 230 and an end effector 232. The first rotary actuator 230 is adapted to rotate the first linkage arm 228 and end effector 232 in a plane perpendicular to the z axis (x-y plane). The first rotary actuator 230 is connected to a second rotary actuator 234 by a second linkage arm 236. The second actuator 234 is adapted to rotate the first actuator 230 in the x-y plane. The second rotary actuator 234 is connected to a third rotary actuator 238 by a third linkage arm 240. The third rotary actuator 238 is connected to the output shaft of the linear actuator 224 and adapted to rotate the second rotary actuator 234 in the x-y plane. The rotary actuators are preferably electric motors with output shafts attached to the respective linkage arms. The actuators 230, 234 and 238 preferably have gear reduction boxes to increase the torque at the linkage arms relative to the electric motors. The electric motors of the actuators 224, 230, 234 and 238 rotate in response to output signals provided by the computer 220.

Figure 13:
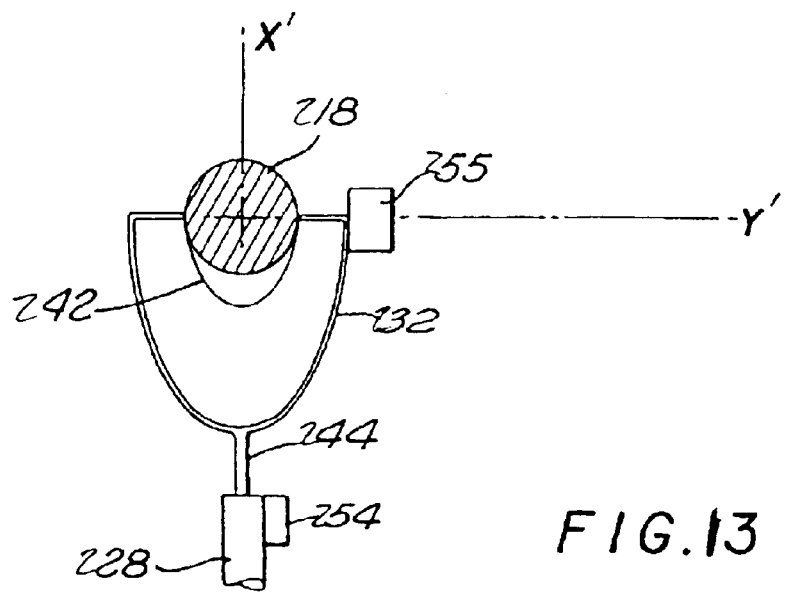
FIG. 13 is a top view of an end effector used to hold an endoscope.

As shown in FIG. 13, the end effector 232 has a clamp 242 which can grasp and hold the endoscope 218. The clamp 242 may be constructed as a wire with a loop that has a diameter smaller than the outside diameter of the scope 218. The clamp 242 allows the scope to be easily attached to and removed from the robotic arm assembly 216. Although a simple wire clamp is shown and described, it is to be understood that the end effector 232 may have any means required to secure the surgical instrument 218. As shown in FIGS. 11 and 12, the junction of the endoscope 218 and the end effector 232 define a second coordinate system which has an x' axis, a y' axis and a z' axis. The end of the endoscope within the patient is located in a third coordinate system which has an x" axis, a y" axis and a z" axis.

The end effector 232 has a shaft 244 which can be coupled to the first linkage arm 228. The first linkage arm 228 may have a bearing which allows the end effector 232 to rotate about the longitudinal axis of the arm 228. The end effector 232 may be constructed so that the clamp 242 and scope 218 can rotate about the y' axis. The end effector 232 is preferably constructed to be detached from the first linkage arm 228, so that a sterile instrument can be used for each surgical procedure. The robotic system 210 may also have a bag or cover to encapsulate the robotic arm assembly 216 to keep the assembly 16 sterile.

The actuators 224, 230, 234 and 238 may each have position sensors 246–252 that are connected to the computer 220. The sensors may be potentiometers that can sense the rotational movement of the electric motors and provide feedback signals to the computer 220.

The end effector 232 may also have a first joint position sensor 254 that senses the angular displacement of the effector about the x' axis and a second joint position sensor 255 which senses the angular displace of the scope about the y' axis.

Figure 14:
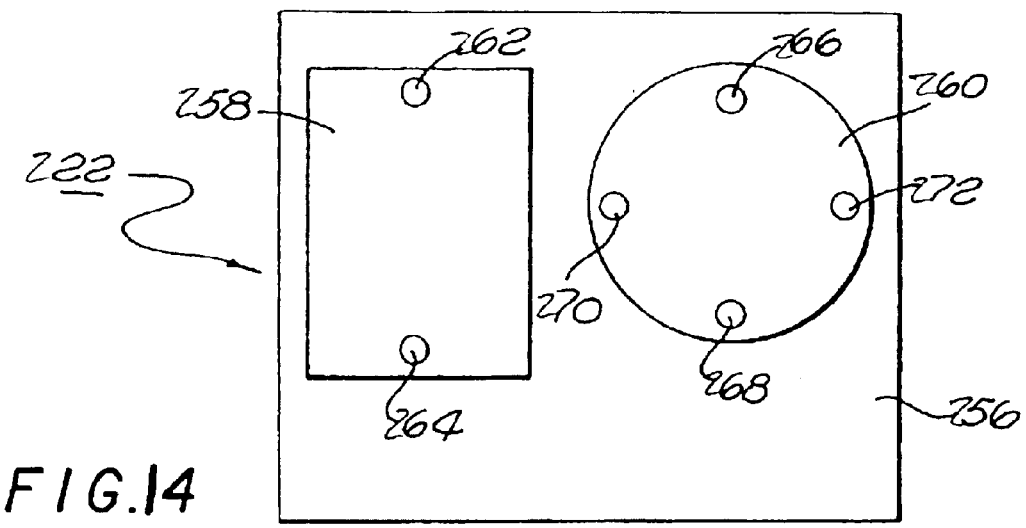
FIG. 14 is a top view of a foot pedal of the system of FIG. 11.
Figure 15:
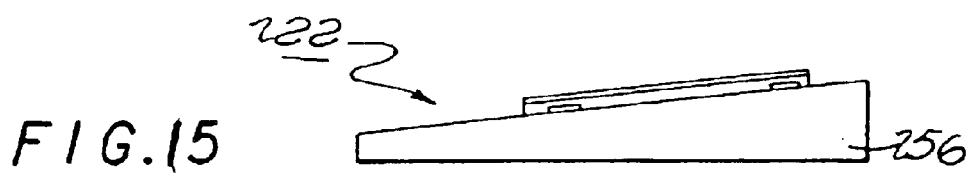
FIG. 15 is a cross-sectional view of the foot pedal of FIG. 14.

FIGS. 14 and 15 show a preferred embodiment of the foot pedal 222. The foot pedal 222 has a housing 256 that supports a first foot switch 258 and a second foot switch 260. The first foot switch 258 has a first pressure transducer 262 and a second pressure transducer 264. The second foot switch 260 has third 266, fourth 268, fifth 270 and sixth 272 pressure transducers. The transducers are each connected to a corresponding operational amplifier that provides a voltage input to the computer 220. The pressure transducers 262–272 are constructed so that the resistance of each transducer decreases as the surgeon increases the pressure on the foot switches. Such a transducer is sold by INTERLINK ELECTRONICS. The decreasing transducer resistance increases the input voltage provided to the computer 220 from the operational amplifier. Each transducer corresponds to a predetermined direction in the third coordinate system. In the preferred embodiment, the first pressure transducer 262 corresponds to moving the endoscope toward the image viewed by the surgeon. The second transducer 64 moves the scope away from the image. The third 266 and fourth 268 transducers move the scope 218 "up" and "down", respectively, and the fifth 270 and sixth 272 transducers move the scope 218 "left" and "right", respectively.

Figure 16:
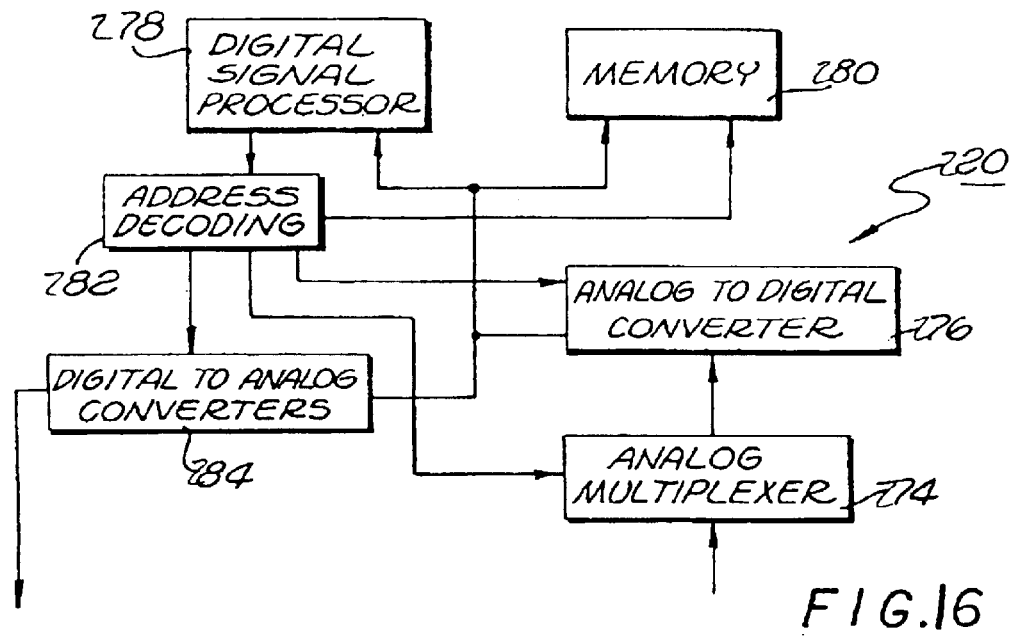
FIG. 16 is a schematic of a computer of the robotic system shown in FIG. 11.

FIG. 16 shows a schematic of the computer 220. The computer 220 has a multiplexer 274 which is connected to the pressure transducers and the position sensors. In the preferred embodiment, the multiplexer 274 has 212 channels, one channel for each sensor and transducer. The multiplexer 274 is connected to a single analog to digital (A/D) converter 276.

The computer also has a processor 278 and memory 280. The A/D converter 276 is constructed so that the converter can provide the processor 278 with a binary string for each voltage level received from the input signals of the system. By way of example, the transducers may provide a voltage ranging between 0–10 volts (V) and the converter 276 may output a different 212 bit binary string for each voltage level. An input signal of 1.0 V may correspond to the binary string 000011001010, 2.0 V may correspond to 000111010100 and so forth and so on.

The processor 278 is connected to an address decoder 282 and four separate digital to analog (D/A) converters 284. Each D/A converter is connected to an actuator 226, 230, 234 or 238. The D/A converters 284 provide analog output signals to the actuators in response to output signals received from the processor 278. The analog output signals preferably have a sufficient voltage level to energize the electric motors and move the robotic arm assembly. The D/A converters 284 may be constructed so that a binary 1 from the processor produces an analog output signal that drives the motors. In such an embodiment, the motors are energized for as long as the processor provides a binary 1 output signal. The decoder 282 correlates the addresses provided by the processor with a corresponding D/A converter, so that the correct motor(s) is driven. The address decoder 282 also provides an address for the input data from the A/D converter so that the data is associated with the correct input channel.

The processor 278 computes the movement of the robotic arm assembly 16 in accordance with the following algorithms.

$$a3 = \pi - \cos^{-1}\left(\frac{(x - 13\cos(\pi))^2 + 13\sin(\pi))^2 - L1^2 - L2^2}{2L1L2}\right)$$

$$\Delta = \cos^{-1}\left(\frac{\begin{array}{c}(x - 13\cos(\pi))^2 + (y - 13\cos(\pi))^2 + \\ (y - 13\sin(\pi))^2 - L1^2 - L2^2\end{array}}{2L1\sqrt{(x - 13\cos(\pi))^2 + (y - 13\sin(\pi))^2}}\right)$$

$$a0 = \tan^{-1}2\left(\frac{y - L3\sin(\pi)}{x - 13\sin(\pi)}\right)$$

$$a2 = a0 + 1 - \Delta$$

$$a4 = \pi - a2 - a3$$

where;

a2=angle between the third linkage arm and the x axis.

a3=angle between the second linkage arm and the longitudinal axis of the third linkage arm.

a4=angle between the first linkage arm and the longitudinal axis of the second linkage arm.

L1=length of the third linkage arm.

L2=length of the second linkage arm.

L3=length of the first linkage arm.

π=the angle between the first linkage arm and the x' axis of the second coordinate system.

x=x coordinate of the end effector in the first coordinate system.

y=y coordinate of the end effector in the first coordinate system. To move the end effector to a new location the processor 278 computes the change in angles a2, a3 and a4, and then provides output signals to move the actuators accordingly. The original angular position of the end effector is provided to the processor 278 by the sensors 246–255. The processor moves the linkage arms an angle that corresponds to the difference between the new location and the original location of the end effector. The differential angle Δa2 corresponds to the amount of angular displacement provided by the third actuator 238, the differential angle Δa3 corresponds to the amount of angular displacement provided by the second actuator 234 and the differential angle Δa4 corresponds to the amount of angular displacement provided by the first actuator 230.

To improve the effectiveness of the system 10, the system is constructed so that the movement of the surgical instrument as seen by the surgeon, is always in the same direction as the movement of the foot pedal. Thus when the surgeon presses the foot switch to move the scope up, the scope always appears to move in the up direction. To accomplish this result, the processor 278 converts the desired movement of the end of the endoscope in the third coordinate system to coordinates in the second coordinate system, and then converts the coordinates of the second coordinate system into the coordinates of the first coordinate system.

The desired movement of the endoscope is converted from the third coordinate system to the second coordinate system by using the following transformation matrix;

$$\begin{pmatrix}\Delta x' \\ \Delta y' \\ \Delta z'\end{pmatrix} = \begin{pmatrix}\cos(a6) & 0 & -\sin(a6) \\ -\sin(a5)\sin(a6) & \cos(a5) & -\sin(a5)\cos(a6) \\ \cos(a5)\sin(a6) & \sin(a5) & \cos(a5)\cos(a6)\end{pmatrix}\begin{pmatrix}\Delta x'' \\ \Delta y'' \\ \Delta z''\end{pmatrix}$$

where;

Δx"=the desired incremental movement of the scope along the x" axis of the third coordinate system.

Δy"=the desired incremental movement of the scope along the y" axis of the third coordinate system.

Δz"=the desired incremental movement of the scope along the z" axis of the third coordinate system.

a5=the angle between the scope and a x'-z' plane the second coordinate system.

a6=the angle between the scope and a y'-z' plane the second coordinate system.

Δ'=the computed incremental movement of the scope along the x' axis of the second coordinate system.

Δy'=the computed incremental movement of the scope along the y' axis of the second coordinate system.

Δz'=the computed incremental movement of the scope along the z' axis of the second coordinate system.

Figure 17:
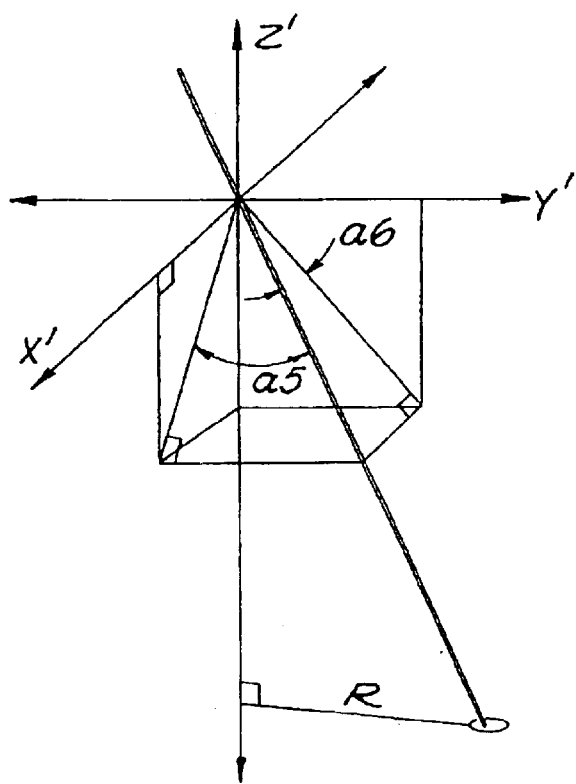
FIG. 17 is a schematic of the endoscope oriented in a second coordinate system.

The angles a5 and a6 are provided by the first 254 and second 255 joint position sensors located on the end effector 232. The angles a5 and a6 are shown in FIG. 17.

The desired movement of the endoscope is converted from the second coordinate system to the first coordinate system by using the following transformation matrix;

$$\begin{pmatrix}\Delta x \\ \Delta y \\ \Delta z\end{pmatrix} = \begin{pmatrix}\cos(\pi) & -\sin(\pi) & 0 \\ \sin(\pi) & \cos(\pi) & 0 \\ 0 & 0 & 1\end{pmatrix}\begin{pmatrix}\Delta x' \\ \Delta y' \\ \Delta z'\end{pmatrix},$$

where;

Δx'=the computed incremental movement of the scope along the x' axis of the second coordinate system.

Δy'=the computed incremental movement of the scope along the y' axis of the second coordinate system.

Δz'=the computed incremental movement of the scope along the z' axis of the second coordinate system.

π=is the angle between the first linkage arm and the x axis of the first coordinate system.

Δx=the computed incremental movement of the scope along the x axis of the first coordinate system.

Δy=the computed incremental movement of the scope along the y axis of the first coordinate system.

Δz=the computed incremental movement of the scope along the z axis of the first coordinate system. The incremental movements Δx and Δy are inserted into the algorithms (1) described above for computing the angular movements (Δa2, Δa3 and Δa4) of the robotic arm assembly to determine the amount of rotation that is to be provided by each electric motor. The value Δz is used to determine the amount of linear movement provided by the linear actuator 226.

After each movement of the endoscope a new π value must be computed. Because the scope is in the y'-z' plane, the π value only changes when the end effector is moved along the x' axis. The new π angle is computed with the following algorithms:

$$d = \left|\frac{m}{\tan(a6)}\right|$$

$$r = |d \sin(a5)|$$

$$\Delta\pi = \tan^{-1}\frac{m}{r}$$

Δπ=tan$^{-1}$m/r where;

d=the length of the endoscope between the end effector and the cannula pivot point.

r=the distance along the y' axis between the end effector and the cannula pivot point.

m=the incremental movement of the scope.

The new π value is computed and stored in the memory of the computer for further computation.

Figure 18:
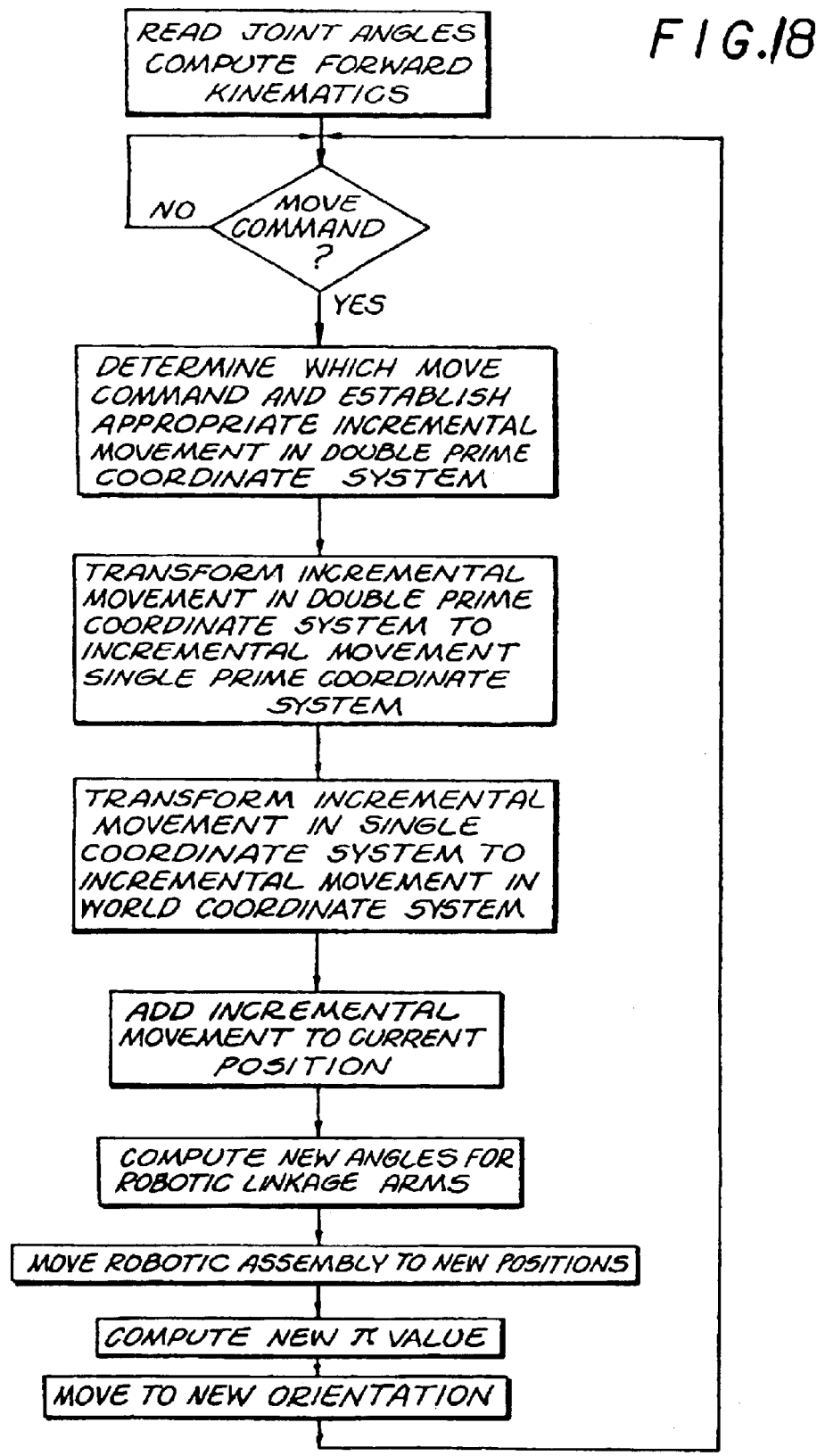
FIG. 18 is a flowchart showing the operation of the system.

FIG. 18 shows a flowchart of a program used to operate the system. The computer 220 initially computes the location of the end effector 232 with the input provided by the sensors 246–255. When the surgeon presses on one of the foot switches, the pedal provides a input signal to the computer. For example, the surgeon may want a closer look at an object in front of the endoscope. The surgeon then presses the top of the first foot switch, depressing the first transducer and providing an input signal to the computer. The input signal is converted into an 12 bit binary string which is received by the processor. The 12 bit string corresponds to a predetermined increment of $\Delta z''$. The computer is constantly sampling the foot pedal, wherein each sample corresponds to a predetermined increment in the corresponding axis". If the surgeon holds down the foot pedal during two sampling periods then the increment to be moved is $2 \times \Delta z''$. The converter also provides a multiplication factor for each increase in voltage level received from the amplifier of the transducer, so that the increments are increased for each increase in voltage. Thus the surgeon can increase the amount of incremental movement by increasing the pressure on the foot switch.

The processor 278 then computes the coordinates in the second coordinates system. The incremental movements in the third coordinate system ($\Delta x''$, $\Delta y''$ and $\Delta z''$) are used to compute the increment movements in the second coordinate system ($\Delta x'$, $\Delta y'$ and $\Delta z'$) and the coordinates in the first coordinate system ($\Delta x$, $\Delta y$ and $\Delta z$). The incremental movements are then used to determine the change in the angles a2, a3 and a4. The computer provides output signals to the appropriate electric motors to move the robotic arm assembly to the new position. The new π angle is computed and the process is repeated. The present invention thus allows the surgeon to remotely move a surgical instrument in a manner that directly correlates with the viewing image seen through the endoscope.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A system that allows a user to control a movement of an endoscope, the endoscope being located within an endoscope coordinate system that has a left-right axis and an up-down axis which are orthogonal to each other and to a longitudinal axis of the endoscope, comprising:
    a robotic arm linkage located in a world coordinate system and supporting the endoscope;
    a display showing a viewing image taken by the endoscope, the display located in the world coordinate system and the viewing image taken in the endoscope coordinate system;
    a first actuator coupled to said robotic arm;
    a second actuator that is coupled to said robotic arm, said first and second actuators being capable of moving the endoscope;
    an input device that can receive a command from the user to effect a commanded movement of the endoscope along the up-down axis in the endoscope coordinate system;
    a controller that receives the user command, the controller computing a transformation of the commanded movement of the endoscope in the endoscope coordinate system to a movement of the endoscope in the world coordinate system, and provides output signals to said first and second actuators to move the endoscope in the world coordinate system so that the endoscope moves along the up-down axis.

2. The system of claim 1, further comprising a third actuator coupled to said robotic arm.

3. The system of claim 1, further comprising an end effector that is coupled to said controller and spins the endoscope.

4. The system of claim 1, wherein said input device comprises a foot pedal.

5. The system of claim 1, wherein said first and second actuators include electric motors.

6. The system of claim 1, further comprising a first position sensor coupled to said first actuator and a second position sensor coupled to said second actuator.

7. The system of claim 1, wherein said controller transforms the desired movement of the endoscope in the endoscope coordinate system to movement of the endoscope in the world coordinate system in accordance with a plurality of transformation equations.

8. The system of claim 1, further comprising a table that is coupled to said first and second actuators.

9. A medical system that can be controlled by a user, comprising:
    a display showing a viewing image, the display located in a world coordinate system;
    a first actuator;
    a second actuator;
    an endoscope that is coupled to said first and second actuators, said endoscope being located within an endoscope coordinate system that bas an x axis and a y axis which are orthogonal to each other, and to a longitudinal axis of the endoscope, said endoscope capturing the viewing image so that the viewing image shown in the display has the endoscope coordinate system;
    an input device that can receive a command from the user to move the endoscope along the y axis in the endoscope coordinate system; and
    a controller that receives the user command and computes a transformation of the command from the endoscope coordinate system to a movement of the endoscope in the world coordinate system, and provides output signals to said first and second actuators to move the endoscope in the world coordinate system to that the endoscope moves along the y axis.

10. The system of claim 9, further comprising a third actuator coupled to said endoscope.

11. The system of claim 9, further comprising an end effector that is coupled to said controller and spins the endoscope.

12. The system of claim 9, wherein said input device comprises a foot pedal.

13. The system of claim 9, wherein said first and second actuators include electric motors.

14. The system of claim 9, further comprising a first position sensor coupled to said first actuator and a second position sensor coupled to said second actuator.

15. The system of claim 9, wherein said controller transforms the movement of the endoscope in the endoscope coordinate system to movement of the endoscope world coordinate system in accordance with a plurality of transformation equations.

16. The system of claim 9, further comprising a table that is coupled to said first and second actuators.

17. The system of claim 1, wherein the controller computes the transformation by computing a first transformation of the commanded movement from an endoscope coordinate system to an intermediate coordinate system, and by computing a second transformation of the commanded movement from the intermediate coordinate system to the world coordinate system.

18. The system of claim 1, further comprising a first robotic instrument arm having first and second instrument actuators and holding a first surgical instrument, the input device comprising a first handle movable in the world coordinate system to input a first instrument command, the controller coupled to the first robotic instrument arm and calculating signals for the first and second instrument actuators.

19. The system of claim 18, further comprising a second robotic instrument arm having third and fourth instrument actuators and holding a second surgical instrument, the input device comprising a second handle movable in the world coordinate system to input a second instrument command, the controller coupled to the second robotic instrument arm and calculating signals for the third and fourth instrument actuators.

20. The system of claim 18, wherein the controller stores a pivot point location along a shaft of the first instrument, and wherein the controller calculate the signals for the first and second instrument actuators using the pivot point location.

21. The system of claim 20, wherein the controller updates the pivot point location and issues a warning signal if movement of the pivot point exceeds a threshold value.

* * * * *